US011851711B2

(12) United States Patent
Vrba et al.

(10) Patent No.: US 11,851,711 B2
(45) Date of Patent: Dec. 26, 2023

(54) DNA METHYLATION BIOMARKERS FOR CANCER DIAGNOSING

(71) Applicant: ARIZONA BOARD OF REGENTS ON BEHALF OF THE UNIVERSITY OF ARIZONA, Tucson, AZ (US)

(72) Inventors: Lukas Vrba, Tucson, AZ (US); Bernard W. Futscher, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 480 days.

(21) Appl. No.: 16/651,871

(22) PCT Filed: Oct. 1, 2018

(86) PCT No.: PCT/US2018/053737
§ 371 (c)(1),
(2) Date: Mar. 27, 2020

(87) PCT Pub. No.: WO2019/068082
PCT Pub. Date: Apr. 4, 2019

(65) Prior Publication Data
US 2020/0255904 A1    Aug. 13, 2020

Related U.S. Application Data

(60) Provisional application No. 62/566,105, filed on Sep. 29, 2017.

(51) Int. Cl.
*C12Q 1/68* (2018.01)
*C07H 21/04* (2006.01)
*C12Q 1/6886* (2018.01)

(52) U.S. Cl.
CPC ..... *C12Q 1/6886* (2013.01); *C12Q 2600/154* (2013.01)

(58) Field of Classification Search
None
See application file for complete search history.

(56) References Cited

U.S. PATENT DOCUMENTS

| 2009/0208930 A1 | 8/2009 | Bergmann |
| 2015/0119350 A1 | 4/2015 | Kebebew |
| 2016/0210403 A1* | 7/2016 | Zhang ............... G16B 40/20 |
| 2017/0175205 A1 | 6/2017 | Toung |
| 2022/0251663 A1 | 8/2022 | Futscher |

FOREIGN PATENT DOCUMENTS

| WO | 2012167145 | 12/2012 |
| WO | 2016115530 | 7/2016 |
| WO | WO-2016115530 A1 * | 7/2016 ........... C12Q 1/6886 |
| WO | 2016207656 | 12/2016 |
| WO | 2019068082 | 4/2019 |

OTHER PUBLICATIONS

GSM1465025 (Sep. 10, 2014). (Year: 2014).*
International Search Report anf Written Opinion for corresponding PCT application PCT/US18/53737 dated Jan. 24, 2019.
Vrba, et al., "DNA methylation changes in biomarker loci occur early in cancer progression", F1000Research, 8(2106):1-9 (2019b).
Vrba, et al., "DNA methylation biomarkers discovered in silico detect cancer in liquid biopsies from non-small cell lung cancer patients", Epigenetics, 15(4):21-28 (2019a).

* cited by examiner

Primary Examiner — Jeanine A Goldberg
(74) Attorney, Agent, or Firm — PABST PATENT GROUP LLP

(57) ABSTRACT

Cancer specific DNA methylation regions have been studied to find cancer specific DNA methylation markers for most common cancers. Differentially methylated regions for individual cancer types were identified and those were further filtered against data from normal tissues to obtain marker regions with cancer specific methylation, resulting in total of 1,250 hypermethylated and 584 hypomethylated marker CpGs. Optimal sets of six markers for each TCGA cancer type that could identify most tumors with high specificity and sensitivity (AUC 0.969-1.00) were chosen from hypermethylated markers and a universal 12 marker set that can detect tumors of all 33 TCGA cancer types (AUC>0.84) was also chosen from hypermethylated markers.

9 Claims, 10 Drawing Sheets
Specification includes a Sequence Listing.

FIG. 1

TCGA Illumina HumanMethylation450 data:
33 cancer types (total 8,566 tumors)
23 with normal samples (total 746 normals)
485,512 array probes
291,604 total probes used after filtering DMRs for each of 23 cancers vs respective normal:
34,878 CpGs in hypermethylated DMRs
23,351 CpGs in hypomethylated DMRs
57,474 total probes in DMRs DMRs filtered against TCGA (n=746)
and GEO (n=2,189) normal tissue samples,
only the best CpG per filtered DMR kept:
18 cancer types with any hypermethylated markers
19 cancer types with any hypomethylated markers
1,250 total hypermethylated marker CpGs
584 total hypomethylated marker CpGs
1,834 total marker CpG probes Select optimal hypermethylated marker sets for
each of 18 cancer types to identify most tumors:
90 total individual CpG probes across 18 sets Select optimal universal hypermethylated marker
set to identify most tumors in any cancer type:
12 CpG probes Validate selected marker sets using independent
tumor and normal data cohorts from GEO:
738 additional HumanMethylation450 samples
27 WGBS-seq samples

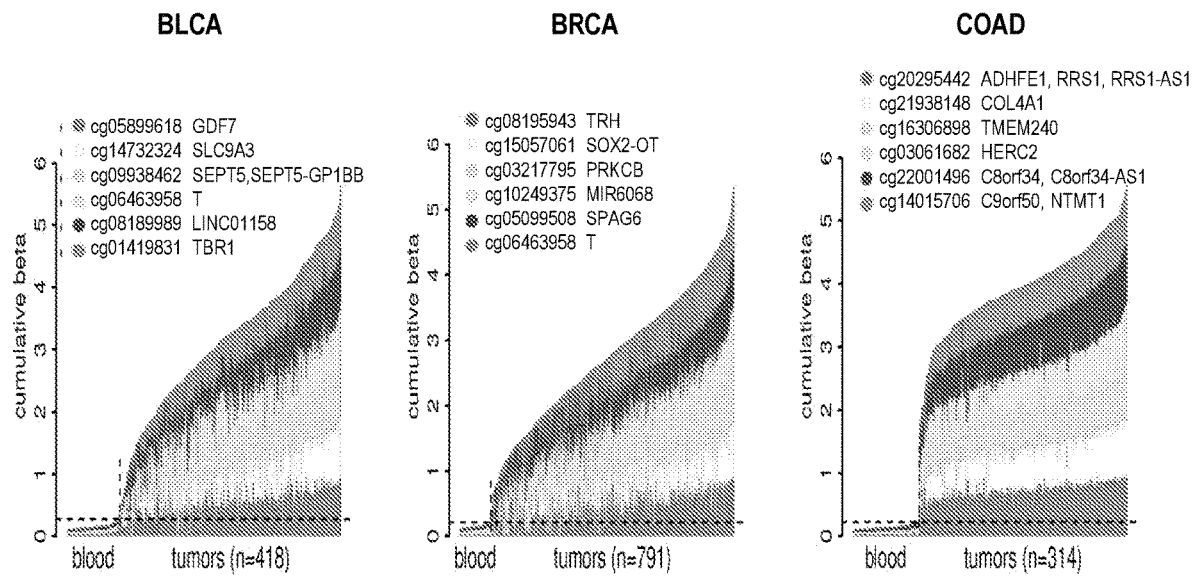
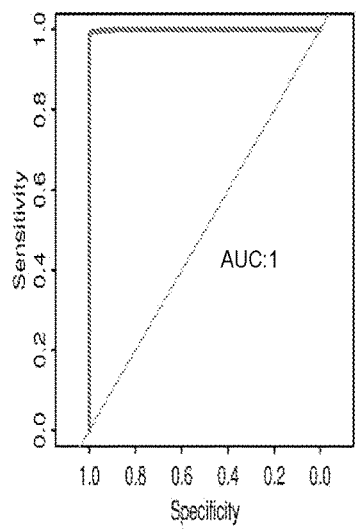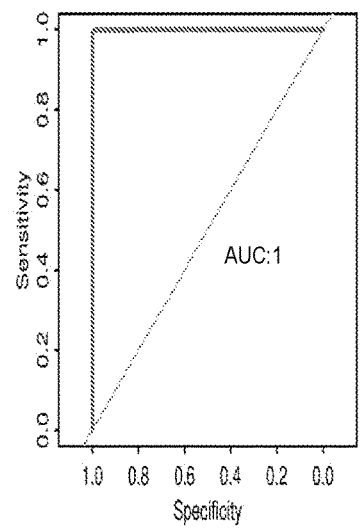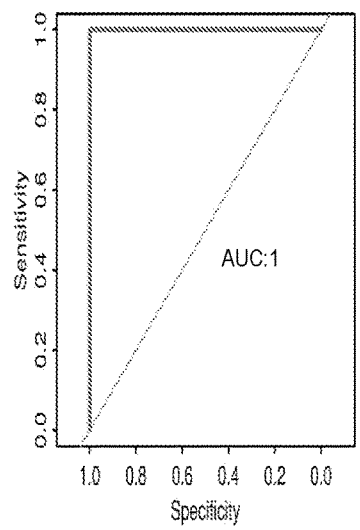
FIG. 3A

FIG. 7

Two-step qPCR

Fist step: Pre-amplification
one multiplex reaction per sample
Primers: 13 primer pairs (10 markers and 3 control amplicons)
Template: total amount of BS converted cfDNA extracted from 2 ml of plasma
PCR: 15 cycles only

Advantage: all methylated template molecules extracted from 2 ml of plasma are in contact with all primer pairs and therefore amplified (about 10,000 fold)

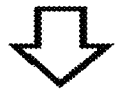

Second step: Quantification
13 individual reactions per sample
Primers: amplicon specific primer pair and probe in each reaction
Template: 5 ul of 200 fold diluted product from the first step
PCR: standard qPCR parameters Advantage: since all the available template was pre-amplified in the first step there is enough copies of each methylated marker to be equally divided into individual marker specific reactions for quantification and therefore could be successfully detected even if the original amount was only several molecules

SEQUENCE LISTING

<160> NUMBER OF SEQ ID NOS: 36

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct

<400> SEQUENCE: 1
gttcggtttt agggttcgga gat                                              23

<210> SEQ ID NO 2
<211> LENGTH: 26
<212> TYPE: DNA
<213> ORGANISM: Artificial Sequence
<220> FEATURE:
<223> OTHER INFORMATION: Synthetic Construct

<400> SEQUENCE: 2
ttttataggg gtagcgatta gcgttg                                      26

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct

<400> SEQUENCE: 3
ggatattgta tgcgtttgcg tagatt                                      26

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
cgggcgaagc gtacggtgt                                              19

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
tgcgttttat cgatcgtacg tgtt                                        24

<210> SEQ ID NO 6
<211> LENGTH: 29
<212> TYPE: DNA
<213> ORGANISM: Artificial Sequence
<220> FEATURE:
<223> OTHER INFORMATION: Synthetic Construct

<400> SEQUENCE: 6
gatttagtag tcgttggtat aagttgcgt                                   29

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
cgtttcggaa tcgacgtgag c                                           21

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
agtgataggt tggttcggcg tagt                                          24

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
cggtcggtta cgtcgtcgaa t                                             21

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
ttgagattgg cggaggcggt t                                             21

<210> SEQ ID NO 11
<211> LENGTH: 25
<212> TYPE: DNA
<213> ORGANISM: Artificial Sequence
<220> FEATURE:
<223> OTHER INFORMATION: Synthetic Construct

<400> SEQUENCE: 11
ttgtatttga cgggtaattt gagcg                                         25

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
gggttttagt tcggagcggg t                                             21

<210> SEQ ID NO 13
<211> LENGTH: 20
<212> TYPE: DNA
<213> ORGANISM: Artificial Sequence
<220> FEATURE:
<223> OTHER INFORMATION: Synthectic Construct

<400> SEQUENCE: 13
ggtgacggtt gggggcgtat                                               20

<210> SEQ ID NO 14
<211> LENGTH: 26
<212> TYPE: DNA
<213> ORGANISM: Artificial Sequence
<220> FEATURE:
<223> OTHER INFORMATION: Synthetic Construct

<400> SEQUENCE: 14
caaaatatac cgacttcttc gattcg                                        26

<210> SEQ ID NO 15

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
ctctaaaacg cgctcaccga aa                                              22

<210> SEQ ID NO 16
<211> LENGTH: 28
<212> TYPE: DNA
<213> ORGANISM: Artificial Sequence
<220> FEATURE:
<223> OTHER INFORMATION: Synthetic Construct

<400> SEQUENCE: 16
cataacaaca acgtacctct acgtcctc                                        28

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
cgcaaaataa ctaacccgac tacga                                           25

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
cccgactacg ctcctccgac                                                 20

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
cgataaatcc gcgcactcga a                                               21

<210> SEQ ID NO 20
<211> LENGTH: 22
<212> TYPE: DNA
<213> ORGANISM: Artificial Sequence
<220> FEATURE:
<223> OTHER INFORMATION: Synthetic Construct

<400> SEQUENCE: 20
aaattcgact ccgaacgaac ga                                              22

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct

<400> SEQUENCE: 21
```

```
ctcgcgctac ccccgaaa                                                    18

<210> SEQ ID NO 22
<211> LENGTH: 24
<212> TYPE: DNA
<213> ORGANISM: Artificial Sequence
<220> FEATURE:
<223> OTHER INFORMATION: Synthetic Construct

<400> SEQUENCE: 22
caacgaaacg aaaacgatta cgaa                                             24

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23
ccattttctt ttaaacgaaa ctcgc                                            25

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
cttaaaacgt ttaaactccc gcaac                                            25

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
gaccaaaacg accccgaaca a                                                21

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct

<400> SEQUENCE: 26
aaaatacgcc aaccgcatac ga                                               22

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
tttgggtcgg gttgggtcgt tt                                               22

<210> SEQ ID NO 28
<211> LENGTH: 29
<212> TYPE: DNA
```

```
<213> ORGANISM: Artificial Sequence
<220> FEATURE:
<223> OTHER INFORMATION: Synthetic Construct

<400> SEQUENCE: 28
tcgttttcgt agttagagag gttcggatg                               29

<210> SEQ ID NO 29
<211> LENGTH: 24
<212> TYPE: DNA
<213> ORGANISM: Artificial Sequence
<220> FEATURE:
<223> OTHER INFORMATION: Synthetic Construct

<400> SEQUENCE: 29
cggagacgtg ggagcgtttt tttg                                    24

<210> SEQ ID NO 30
<211> LENGTH: 19
<212> TYPE: DNA
<213> ORGANISM: Artificial Sequence
<220> FEATURE:
<223> OTHER INFORMATION: Synthetic Construct

<400> SEQUENCE: 30
tcggttcgtg gaggcggtt                                          19

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
aaccctaccg ccgcacccgc t                                       21

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct

<400> SEQUENCE: 32
cgttatgggt tttttttcgt attcgtatgt                              30

<210> SEQ ID NO 33
<211> LENGTH: 21
<212> TYPE: DNA
<213> ORGANISM: Artificial Sequence
<220> FEATURE:
<223> OTHER INFORMATION: Synthetic Construct

<400> SEQUENCE: 33
tgtgggcggt tacgtgttgc g                                       21

<210> SEQ ID NO 34
<211> LENGTH: 30
<212> TYPE: DNA
<213> ORGANISM: Artificial Sequence
<220> FEATURE:
<223> OTHER INFORMATION: Synthetic Construct

<400> SEQUENCE: 34
ggagaataat cgttatatcg ttatcgacgg                              30
```

```
<210> SEQ ID NO 35
<211> LENGTH: 24
<212> TYPE: DNA
<213> ORGANISM: Artificial Sequence
<220> FEATURE:
<223> OTHER INFORMATION: Synthetic Construct

<400> SEQUENCE: 35
tttggcgagg aaggtatggt cggt                                          24

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
ggtagtagat gttgcgggtg tcggt                                         25
```

DNA METHYLATION BIOMARKERS FOR CANCER DIAGNOSING

CROSS-REFERENCE TO RELATED APPLICATIONS

The application incorporates by reference and claims priority to U.S. Provisional Patent Application Ser. No. 62/566,105, filed on Sep. 29, 2017.

STATEMENT REGARDING FEDERALLY SPONSORED RESEARCH OR DEVELOPMENT

This invention was made with government support under Grant No. P30 CA023074, awarded by NIH. The government has certain rights in the invention.

BACKGROUND

Cancer is the second most common cause of death worldwide. Earlier detection of cancer or its recurrence could improve the treatment and management of the disease. Therefore, to allow frequent cancer screening, techniques for minimally invasive and cost effective cancer diagnosis and monitoring are needed. Biomarkers based on cell-free nucleic acids that could be extracted from blood samples or other liquid biopsies have grown in importance in recent years. When tumor cells die, their DNA is released into a bloodstream, and becomes part of cell-free DNA (cfDNA), which is mostly fragmented to a single nucleosome size and can be recovered from serum and plasma samples. While cfDNA from healthy individuals is comprised mostly of DNA released by dead hematopoietic cells, cfDNA from individuals with cancer contains additionally DNA derived from tumor cells. The fraction of tumor DNA in cfDNA might be substantial and varies from cancer to cancer. The total amount of cfDNA in plasma is relatively low and variable; only about 10 ng/ml plasma in healthy individuals. Sensitive techniques like next generation sequencing or real-time PCR can detect tumor specific DNA changes in cfDNA samples from cancer patients. These tumor specific DNA changes include gene mutations, loss of heterozygosity, translocations and DNA methylation. Detection of specific DNA mutations present in certain tumors could be used for noninvasive monitoring of patients during and after treatment.

SUMMARY

DNA methylation is an optional epigenetic modification of cytosine residues in a sequence context CpG. There are about 28 million CpGs in the human genome. These CpGs are distributed non-randomly and a large fraction of CpGs is located in CpG rich regions called CpG islands. CpG islands are located predominantly at gene promoters and other regulatory regions. In normal cells most of the CpGs are methylated with the exception of CpG islands. Tumor cells have altered epigenome with global DNA hypomethylation and promoter and CpG island specific DNA hypermethylation.

Detection of this cancer specific aberrant DNA methylation in cfDNA samples provides one endpoint for noninvasive cancer diagnostics and monitoring. Multiple DNA regions are typically aberrantly methylated in a majority of tumors and thus DNA methylation could be superior as a cancer specific marker to DNA mutations since very few specific mutations are present in a large fraction of tumors. Therefore detection of DNA methylation of several frequently aberrantly methylated regions may provide higher sensitivity over detecting single or few mutation markers. The cfDNA yield from a typical blood sample is sufficient to perform targeted analysis of several selected marker regions for the presence of cancer specific aberrant DNA methylation. Real-time qPCR or digital droplet PCR (ddPCR) are sensitive enough to detect presence of even small fraction of methylated tumor DNA in a cfDNA sample.

Embodiments of the current technology disclose a method of processing a DNA-containing sample, as well as to detecting or diagnosing one or more types of cancer from a plurality of different cancer types, comprising the step of detecting a level of DNA methylation biomarkers from a plurality of DNA methylation markers of a sample from a subject. In some embodiments hereinafter disclosed below, at least six preselected markers are used. In other embodiments, a plurality of ten markers (i.e., cg14416371, cg08189989, cg00100121, cg03306374, cg01419831, cg25875213, cg00339556, cg01893212, cg14732324 and cg07302069) or of twelve DNA methylation markers is used (i.e., cg01419831, cg03217795, cg08189989, cg14416371, cg16306898, cg08195943, cg14587524, cg22538054, cg22524657, cg04066019, cg14326413, and cg03838635).

The method further comprises determining a degree of confidence based on the level of each DNA methylation biomarker of the panel of DNA methylation markers; and determining a cutoff value; wherein when the degree of confidence is higher than the cutoff value, a diagnosis of cancer.

Embodiments of the current technology also disclose a method diagnosing 18 specific type of cancers with detecting a level of a specific panel of DNA methylation markers respectively.

Moreover, methods of monitoring cancer treatment or recurrence, as well as methods of treating cancer based on detecting a type of cancer through methylation biomarkers and then treating the type of cancer detected, are disclosed.

BRIEF DESCRIPTION OF DRAWINGS

The patent application or application file contains at least one drawing executed in color. Copies of this patent or patent application publication with color drawing(s) will be provided by the Office upon request and payment of the necessary fee. The technology disclosed herein will be better understood from a reading of the following detailed description taken in conjunction with the drawings in which like reference designators are used to designate like elements, and in which:

FIG. 1 is a general schema of the application;

FIG. 3A shows examples of cancer specific marker sets for 3 individual cancer types. The figure shows optimal sets of six markers for each of these three cancers: BLCA, BRCA, and COAD. The plots show DNA methylation of each marker set in individual tumor samples in comparison to normal blood samples. Only 100 randomly chosen blood samples are shown. The horizontal dashed line shows the $95^{th}$ percentile of the cumulative DNA methylation of each marker set in the entire control blood cohort (n=1,388). The ROC analysis curves show the difference between each tumor cohort and the whole normal blood cohort (n=1,388) for each marker set.

FIG. 7 shows the principal of the two-step qPCR that was used to analyze marker regions in cfDNA from cancer patients and healthy subjects.

DETAILED DESCRIPTION

Figure 2:
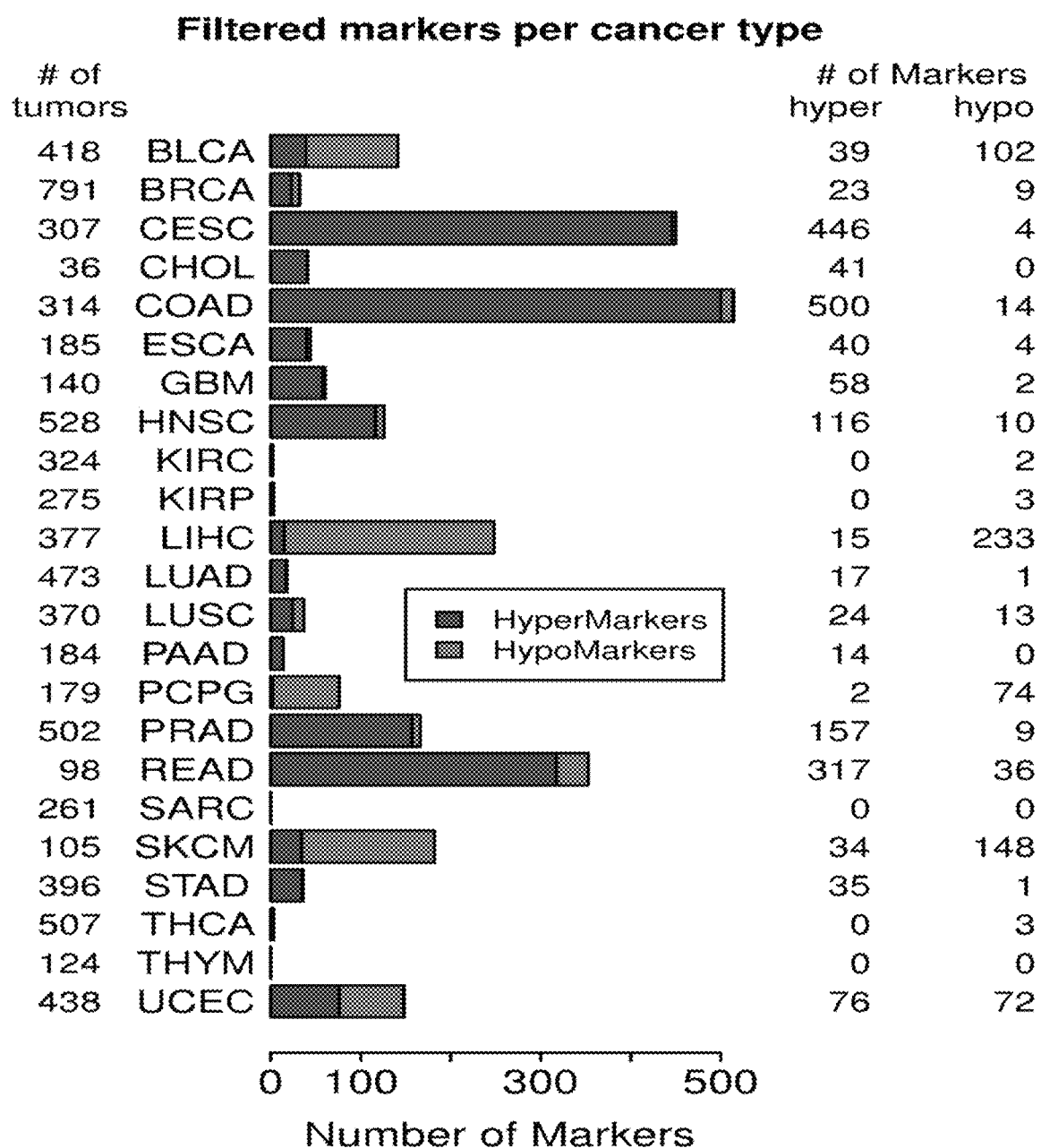
FIG. 2 shows numbers of marker CpGs per cancer. Only 23 TCGA cancer types that had normal samples available and therefore were used in the analysis are displayed. The barplots show the numbers of hypermethylated and hypomethylated marker CpGs per cancer type after filtering.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

In order to diagnose and monitor cancer by detecting cancer specific DNA methylation marker regions, these regions have to be identified first. These marker regions, specifically methylated only in tumor cells, could be identified by the analysis of the whole genome scale DNA methylation data from large cohorts of tumors and normal samples. The most extensive public resource available of such data currently is The Cancer Genome Atlas (TCGA). The TCGA database contains DNA methylation data from Illumina HumanMethylation450 platform from over 8,500 tumor samples of 33 tumor types. In addition Gene Expression Omnibus (GEO) database contains DNA methylation data from the same platform for over 60 thousand samples, including several thousand samples from normal blood and normal tissues. Illumina HumanMethylation450 is a microarray based analytical platform that covers about 450 thousand human CpGs, these CpGs were chosen non-randomly with a focus on CpG islands and gene promoter regions—genomic features that are frequently hypermethylated in cancer. This platform thus provides accurate description of DNA methylation of considerable fraction of individual human CpGs with focus on CpGs likely hypermethylated in tumor cells. The large numbers of samples in TCGA and GEO databases together with substantial coverage of the Illumina HumanMethylation450 platform make these datasets the best possible resource available for discovery of DNA methylation markers across most common cancer types.

TCGA and GEO DNA methylation data were utilized to discover sets of DNA methylation marker regions that could be used for noninvasive diagnostics and monitoring of most cancers. There are a few DNA methylation cancer markers in clinical use today, however, there was no study performed to find DNA methylation markers across the majority of cancers. The present technology analyzed TCGA DNA methylation data to discover sets of new cancer specific DNA methylation markers that can identify most tumor types with high sensitivity and specificity. The whole TCGA Illumina HumanMethylation450 dataset (n=9,312) and several additional Illumina HumanMethylation450 cohorts from GEO (n=2,189) were utilized and analyzed to search for, filter and test cancer specific marker regions. In addition to the known markers like SEPT9 or GSTPJ, over one thousand new marker regions were found across TCGA cancer types. From these markers were then selected optimized sets of six markers for individual cancer types that can identify most tumors of respective type with high sensitivity and specificity (AUC 0.969-1.00). A universal 12 marker set was chosen that can identify tumors from any of 33 TCGA cancer types with AUC 0.84-1.00.

As described herein, sensitivity of a biomarker is defined as a biomarker's ability to detect a disease in patients in whom the disease is truly present (i.e., a true positive), and specificity is the ability to rule out the disease in patients in whom the disease is truly absent (i.e., a true negative).

The invention can be further understood by the following numbered paragraphs:

1. A method of processing a DNA-containing sample from a subject, comprising the steps of processing said DNA-containing sample with a machine-based analytical platform to detect a level of at least six preselected DNA methylation biomarkers.
2. The method of paragraph 1, wherein said at least six preselected DNA methylation biomarkers comprise cg14416371, cg08189989, cg00100121, cg03306374, cg01419831, cg25875213, cg00339556, cg01893212, cg14732324 and cg07302069.
3. The method of paragraph 1, wherein said at least six preselected DNA methylation biomarkers comprise cg01419831, cg03217795, cg08189989, cg14416371, cg16306898, cg08195943, cg14587524, cg22538054, cg22524657, cg04066019, cg14326413, and cg03838635.
4. The method of paragraph 1, wherein said analytical platform comprises one or more of quantitative real time PCR, digital droplet PCR and next gen DNA sequencing.
5. The method of paragraph 1, wherein said DNA-containing sample is chemically-modified with sodium bisulfite and purified prior to processing said DNA-containing sample with a machine-based analytical platform to detect a level of at least six preselected DNA methylation biomarkers.
6. The method of paragraph 1, wherein said DNA is processed to be cell free.
7. A method of detecting one or more cancers from a plurality of different cancer types in a DNA-containing sample from a subject, comprising the step of processing said DNA-containing sample with a machine-based analytical platform to detect a level of at least six preselected DNA methylation biomarkers.
8. The method of paragraph 1, wherein said plurality of different cancer types comprises adrenocortical carcinoma (ACC), urothelial bladder carcinoma (BLCA), breast invasive carcinoma (BRCA), cervical squamous cell carcinoma and endocervical adenocarcinoma (CESC), cholangiocarcinoma (CHOL), colon adenocarcinoma (COAD), lymphoid neoplasm Diffuse Large B-cell Lymphoma (DLBC), esophageal carcinoma (ESCA), glioblastoma multiforme (GBM), head-neck squamous cell carcinoma (HNSC), kidney chromophobe (KICH), kidney renal clear cell carcinoma (KIRC), kidney renal papillary cell carcinoma (KIRP), acute myeloid leukemia (LAML), lower grade glioma (LGG), liver hepatocellular carcinoma (LIHC), lung adenocarcinoma (LUAD), lung squamous cell carcinoma (LUSC), mesothelioma (MESO), ovarian serous cystadenocarcinoma (OV), pancreatic adenocarcinoma (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), testicular germ cell tumors (TGCT), thyroid carcinoma (THCA), thymoma (THYM), uterine corpus endometrial carcinoma (UCEC), uterine carcinosarcoma (UCS), and uveal melanoma (UVM).
9. The method of paragraph 7, wherein the DNA-containing sample is processed to comprise cell free DNA.
10. The method of paragraph 7, wherein said analytical platform comprises one or more of quantitative real time PCR, digital droplet PCR and next gen DNA sequencing.
11. The method of paragraph 7, wherein said DNA-containing sample is chemically-modified with sodium bisulfite and purified prior to processing said DNA-containing sample with a machine-based analytical platform to detect a level of at least six preselected DNA methylation biomarkers.
12. The method of paragraph 1, further including treating a diagnosed cancer by one or more of surgery, chemotherapy, radiation therapy, hormonal therapy, targeted therapy (including immunotherapy such as monoclonal antibody therapy) and synthetic lethality.

13. The method of paragraph 7, further including treating a diagnosed cancer by one or more of surgery, chemotherapy, radiation therapy, hormonal therapy, targeted therapy (including immunotherapy such as monoclonal antibody therapy) and synthetic lethality.
14. The method of paragraph 7, wherein said at least six preselected DNA methylation biomarkers comprise cg14416371, cg08189989, cg00100121, cg03306374, cg01419831, cg25875213, cg00339556, cg01893212, cg14732324 and cg07302069.
15. The method of paragraph 7, wherein said at least six preselected DNA methylation biomarkers comprise cg01419831, cg03217795, cg08189989, cg14416371, cg16306898, cg08195943, cg14587524, cg22538054, cg22524657, cg04066019, cg14326413, and cg03838635.
16. A method of treating one or more cancers from a plurality of different cancer types, comprising the step of processing a DNA-containing sample from a subject with a machine-based analytical platform to detect a level of at least six preselected DNA methylation biomarkers; and
treating a detected cancer by one or more of surgery, chemotherapy, radiation therapy, hormonal therapy, targeted therapy (including immunotherapy such as monoclonal antibody therapy) and synthetic lethality.
17. The method of paragraph 16, wherein the sample comprises cell free DNA
18. A panel of DNA methylation biomarkers comprising cg14416371, cg08189989, cg00100121, cg03306374, cg01419831, cg25875213, cg00339556, cg01893212, cg14732324 and cg07302069 used in a method to detect a type of cancer.

Example 1

To identify cancer-specific DNA methylation markers we utilized the tumor DNA methylation datasets from TCGA. TCGA is the largest publically available resource of gene expression, genetic and epigenetic data from tumor samples. In addition to a large sample numbers the advantage of TCGA data is the consistency between thousands of samples and high standards of quality control. This study used TCGA data from Illumina HumanMethylation450 platform. Data from this platform are presented as beta values—numeric values in interval 0.0-1.0. For unmethylated CpGs beta is approaching zero, for fully methylated CpGs beta is approaching 1 and for CpGs methylated in a fraction of the sample 0<beta<1, e.g. a CpG methylated in 50% of the sample will have beta around 0.5. We used TCGA Illumina HumanMethylation450 data from 8,566 primary tumors of 33 cancer types and from 746 non-tumor tissue samples for 23 cancer types. As the first step towards DNA methylation marker identification, differentially methylated regions (DMRs) were determined for each cancer type for which normal samples were available (FIG. 1).

DMRs are regions where DNA methylation in a group of tested samples is different from a reference. In our particular case the tested samples were all tumors of a certain cancer type and the reference was a group of respective normal tissue samples. DMRs were defined as regions of at least two consecutive CpGs covered by the dataset that are located less than 500 bp apart and have mean difference from respective normal control of at least 0.4 beta (approximately 40% difference in the mean methylation), see Materials and Methods for details. All analyzed cancer types exhibited DMRs of both directions—hyper- and hypo-methylated regions. The numbers of DMRs and the ratio of hyper and hypo methylated regions varied greatly across cancer types with hypermethylated regions being overall more abundant. In summary, as the first step towards cancer-specific marker discovery we identified DMRs for 23 out of 33 TCGA cancer types using TCGA HumanMethylation450 data. Most of the cancer types have hundreds to thousands of differentially methylated regions when compared to their normal tissue counterparts and we predict that some of these DMRs will show tumor specificity making them suitable as marker regions for cancer detection and monitoring.

Identified DMRs marker candidates were filtered against data from normal tissues to reveal cancer specific marker regions aberrantly methylated in large fraction of tumors. Cancer diagnosis from cfDNA samples and other liquid biopsies is typically based on the detection of the presence of a small fraction of the cancer specific aberrant DNA methylation. However, not all identified DMRs are cancer-specific. For example, some DMRs occurring in cancer also occur in some healthy tissues as part of normal physiological means of gene regulation that are frequently co-opted by cancer cells during carcinogenesis. Such DMRs are not suitable as markers since the methylated variant might also be present in the blood of healthy individuals and would result in false positive diagnosis. Therefore the DMR marker candidates were filtered against 18 cohorts of normal tissue samples (n=2,189) from the GEO and normal samples from all TCGA cancer cohorts.

Only regions that were fully unmethylated (for hypermethylated marker candidates) or fully methylated (for hypomethylated marker candidates) across all normal tissue cohorts were selected as cancer markers. Further, a good marker region should be differentially methylated in a large fraction of tumor samples to provide high sensitivity. Therefore, to keep only markers methylated in a majority of tumors, only DMRs differentially methylated by ≥0.25 beta from control in more than ⅔ of tumor samples of the respective cancer type were selected as markers. There were cases where multiple DMRs were located within 2 kb and in such cases only the best performing CpG was selected as a potential marker. The result of the filtering was 18 cancer types that have any hypermethylated and 19 cancer types that have any hypomethylated marker CpGs that passed all the filters (FIG. 2). The total numbers for individual filtered marker CpGs across all cancers were 1,250 hypermethylated and 584 hypomethylated CpGs. The numbers of markers per tumor type ranged up to 500 for hypermethylated marker regions in colon adenocarcinoma (COAD) and up to 233 for hypomethylated marker regions in liver hepatocellular carcinoma (LIHC) (FIG. 2). The hypermethylated DMRs were more common (FIG. 2) likely due to the fact that the platform coverage is biased towards genomic regions hypermethylated in cancer cells. Overall, filtering of DMRs revealed over one thousand of cancer specific DNA methylation marker CpGs, many of them were common across TCGA cancer types.

The next step was to determine optimal combinations of markers for each cancer type that provided maximal sensitivity and specificity. Hypermethylated marker CpGs were more common than hypomethylated ones (FIG. 2) and since they are technically easier to detect, only hypermethylated CpGs were used to select DNA methylation marker sets for the 18 TCGA cancer types that had hypermethylted markers after filtering. The algorithm for marker CpG selection into these sets is described in Materials and Methods. The markers from this study are meant to be used to detect cancer in cfDNA from blood samples and the cfDNA in healthy individuals originates mostly from hematopoietic cells. Therefore a large whole blood cohort from cancer free subjects (n=1388, GSE40279 and GSE87571, 656 and 732 samples, respectively) was used as a normal reference for marker testing to mimic cfDNA from cancer free individuals. The marker sets were then evaluated by two criteria.

First, a tumor was considered to be identified by a marker set if at least one marker in that set had methylation in the respective tumor larger by at least 0.3 beta than the 95th percentile of the control blood cohort. Using this first criterion, selected sets of up to 12 markers were able to identify all of the identifiable tumors in each cancer cohort.

Second, the diagnostic ability of biomarkers is often evaluated by the receiver operating characteristic (ROC) plot and the area under the curve (AUC) of ROC plot; for markers of maximum sensitivity and specificity the AUC is approaching 1.0. Therefore, as the other criterion, we used cumulative beta values of increasing numbers of markers for each cancer type to evaluate the marker sets using the ROC analysis. Sets of six selected markers were able to identify all or majority (>98%) of the identifiable tumors using 0.3 beta cut off and corresponding AUCs were in the range 0.969-1.00 (Table 1) across all 18 cancer types.

TABLE 1

| CancerTyp | TCGA Cancer Type Name | Number of Markers for 100% | Percent Detected with 6 markers | AUC (6 markers cumulative) |
|---|---|---|---|---|
| BLCA | Bladder Urothelial Carcinoma [BLCA] | 6 | 100 | 1 |
| BRCA | Breast invasive carcinoma [BRCA] | 12 | 98.8 | 1 |
| CESC | Cervical squamous cell carcinoma and endocervical adenocarcinoma [CESC] | 3 | 100 | 1 |
| CHOL | Cholangiocarcinoma [CHOL] | 4 | 100 | 1 |
| COAD | Colon adenocarcinoma [COAD] | 2 | 100 | 1 |
| ESCA | Esophageal carcinoma [ESCA] | 3 | 100 | 1 |
| GBM | Glioblastoma multiforme [GBM] | 4 | 100 | 1 |
| HNSC | Head and Neck squamous cell carcinoma | 4 | 100 | 1 |
| LIHC | Liver hepatocellular carcinoma [LIHC] | 7 | 99.7 | 0.996 |
| LUAD | Lung adenocarcinoma [LUAD] | 9 | 98.7 | 0.998 |
| LUSC | Lung squamous cell carcinoma [LUSC] | 7 | 99.4 | 0.997 |
| PAAD | Pancreatic adenocarcinoma [PAAD] | 6 | 100 | 0.969 |
| PCPG | Pheochromocytoma and Paraganglioma [PCPG] | 2 | 100 | 0.999 |
| PRAD | Prostate adenocarcinoma [PRAD] | 6 | 100 | 0.998 |
| READ | Rectum adenocarcinoma [READ] | 2 | 100 | 1 |
| SKCM | Skin Cutaneous Melanoma [SKCM] | 3 | 100 | 1 |
| STAD | Stomach adenocarcinoma [STAD] | 5 | 100 | 1 |
| UCEC | Uterine Corpus Endometrial Carcinoma [UCEC] | 4 | 100 | 1 |

Figure 3B:
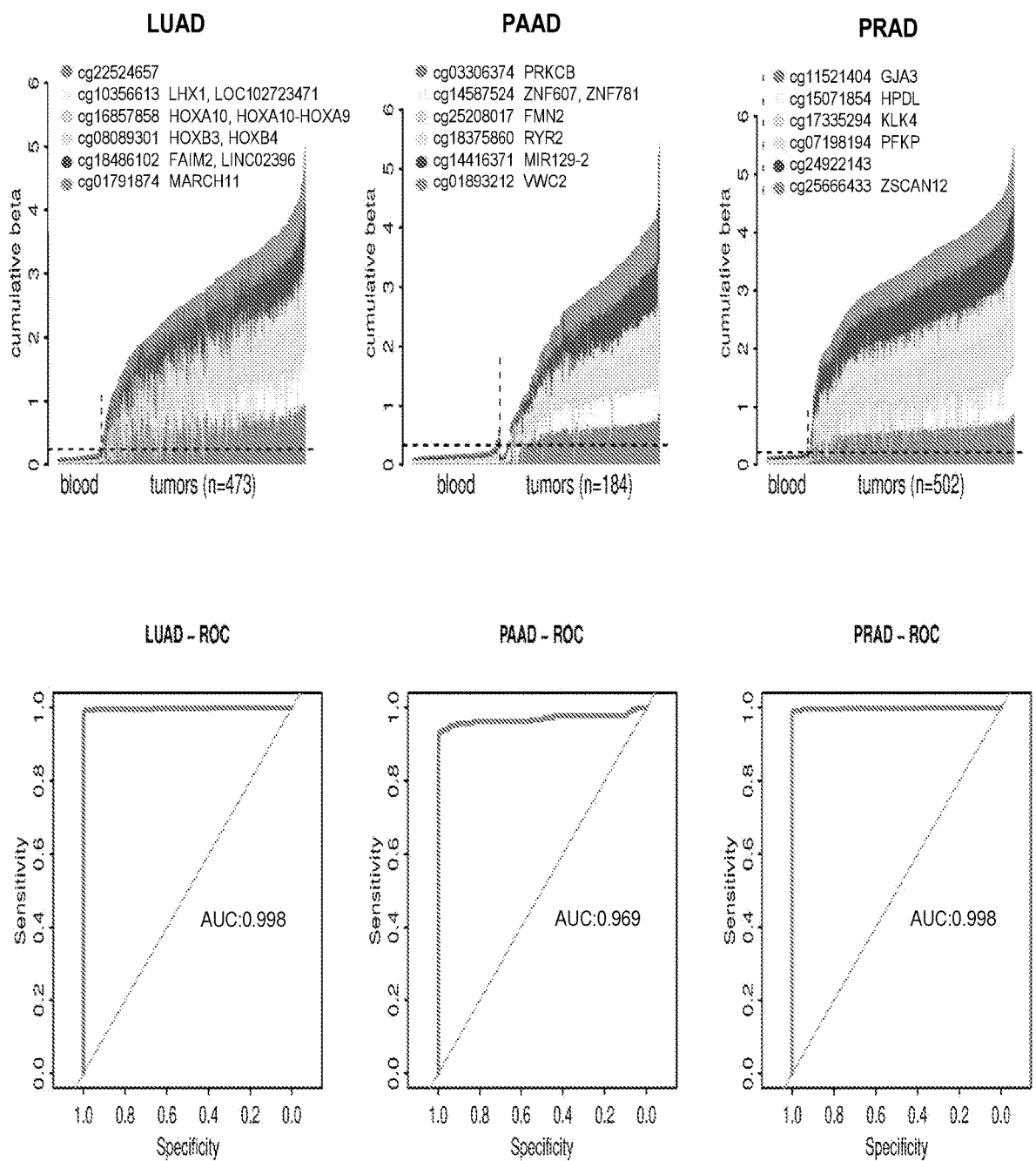
FIG. 3B shows examples of cancer specific marker sets for an additional 3 individual cancer types. The figure shows optimal sets of six markers for each of these three cancers: LUAD, PAAD and PRAD. The plots show DNA methylation of each marker set in individual tumor samples in comparison to normal blood samples. Only 100 randomly chosen blood samples are shown. The horizontal dashed line shows the $95^{th}$ percentile of the cumulative DNA methylation of each marker set in the entire control blood cohort (n=1,388). The ROC analysis curves show the difference between each tumor cohort and the whole normal blood cohort (n=1,388) for each marker set.

Therefore the sets of six markers were chosen as sufficiently large marker sets for individual cancer types. FIG. 3 shows the methylation data for sets of six markers and corresponding ROC curves in breast invasive carcinoma (BRCA), bladder urothelial carcinoma (BLCA), COAD, lung adenocarcinoma (LUAD), pancreatic adenocarcinoma (PAAD), and prostate adenocarcinoma (PRAD). All 18 six marker sets for individual cancer types are listed in Table 2, below

TABLE 2

| Illumina.CpG.ID | CpG.position.hg19 | annotation |
|---|---|---|
| BLCA 6 Marker Set | | |
| cg05899618 | chr2: 20865847-20865848 | GDF7, |
| cg14732324 | chr5: 528621-528622 | SLC9A3, |

TABLE 2-continued

| Illumina.CpG.ID | CpG.position.hg19 | annotation |
|---|---|---|
| cg09938462 | chr22: 19706365-19706366 | SEPT5, SEPT5-GP1BB, |
| cg06463958 | chr6: 166582393-166582394 | T, |
| cg08189989 | chr2: 105459164-105459165 | LINC01158, |
| cg01419831 | chr2: 162283705-162283706 | TBR1, |
| | BRCA 6 Marker Set | |
| cg08195943 | chr3: 129694487-129694488 | TRH, |
| cg15057061 | chr3: 181437299-181437300 | SOX2-OT, |
| cg03217795 | chr16: 23847556-23847557 | PRKCB, |
| cg10249375 | chr1: 63795934-63795935 | MIR6068, |
| cg05099508 | chr10: 22634432-22634433 | SPAG6, |
| cg06463958 | chr6: 166582393-166582394 | T, |
| | CESC 6 Marker Set | |
| cg24403845 | chr10: 108924366-108924367 | SORCS1, |
| cg02230017 | chr16: 6069019-6069020 | RBFOX1, |
| cg05099508 | chr10: 22634432-22634433 | SPAG6, |
| cg00002719 | chr1: 169396706-169396707 | CCDC181, |
| cg15467646 | chr1: 22141014-22141015 | LDLRAD2, |
| cg20718350 | chr12: 103352294-103352295 | ASCL1, |
| | CHOL 6 Marker Set | |
| cg10333808 | chr12: 22487459-22487460 | ST8SIA1, |
| cg16104915 | chr7: 27205217-27205218 | HOXA10-HOXA9, |
| cg09420439 | chr7: 27136424-27136425 | HOTAIRM1, |
| cg25764899 | chr1: 47697948-47697949 | TAL1, |
| cg14458834 | chr17: 46655394-46655395 | HOXB3, HOXB4, |
| cg16405026 | chr2: 145281942-145281943 | LINC01412, LOC105373656, |
| | COAD 6 Marker Set | |
| cg20295442 | chr8: 67344665-67344666 | ADHFE1, RRS1, RRS1-AS1, |
| cg21938148 | chr13: 110958977-110958978 | COL4A1, |
| cg16306898 | chr1: 1475675-1475676 | TMEM240, |
| cg03061682 | chr15: 28352098-28352099 | HERC2, |
| cg22001496 | chr8: 69243486-69243487 | C8orf34, C8orf34-AS1, |
| cg14015706 | chr9: 132382433-132382434 | C9orf50, NTMT1, |
| | ESCA 6 Marker Set | |
| cg13024709 | chr2: 131792772-131792773 | ARHGEF4, |
| cg14416371 | chr11: 43602847-43602848 | MIR129-2, |
| cg16306898 | chr1: 1475675-1475676 | TMEM240, |
| cg14763548 | chr20: 25062447-25062448 | VSX1, |
| cg08189989 | chr2: 105459164-105459165 | LINC01158, |
| cg25875213 | chr19: 38183055-38183056 | ZNF781, |
| | GBM 6 Marker Set | |
| cg14543508 | chr9: 123631308-123631309 | PHF19, |
| cg26970841 | chr16: 85932666-85932667 | IRF8, |
| cg12206199 | chr2: 39187543-39187544 | ARHGEF33, |
| cg06798642 | chr4: 48272082-48272083 | TEC, |
| cg22865720 | chr1: 1981816-1981817 | LOC105378591, PRKCZ, |
| cg04922681 | chr13: 43149234-43149235 | TNFSF11, |
| | HNSC 6 Marker Set | |
| cg17300544 | chr17: 75369091-75369092 | SEPT9, |
| cg14416371 | chr11: 43602847-43602848 | MIR129-2, |
| cg18087672 | chr17: 46824915-46824916 | , |
| cg03978375 | chr16: 85932668-85932669 | IRF8, |
| cg06463958 | chr6: 166582393-166582394 | T, |
| cg09859398 | chr14: 59932033-59932034 | GPR135, |
| | LIHC 6 Marker Set | |
| cg12206199 | chr2: 39187543-39187544 | ARHGEF33, |
| cg13564825 | chr19: 38747201-38747202 | PPP1R14A, |
| cg08162372 | chr14: 54422925-54422926 | BMP4, |
| cg16306898 | chr1: 1475675-1475676 | TMEM240, |
| cg22524657 | chr1: 47999163-47999164 | , |
| cg22538054 | chr12: 95941988-95941989 | USP44, |
| | LUAD 6 Marker Set | |
| cg22524657 | chr1: 47999163-47999164 | , |
| cg10356613 | chr17: 35294491-35294492 | LHX1, LOC102723471, |
| cg16857858 | chr7: 27213984-27213985 | HOXA10, HOXA10-HOXA9, |
| cg08089301 | chr17: 46655561-46655562 | HOXB3, HOXB4, |
| cg18486102 | chr12: 50297777-50297778 | FAIM2, LINC02396, |
| cg01791874 | chr5: 16180055-16180056 | MARCH11, |

TABLE 2-continued

| Illumina.CpG.ID | CpG.position.hg19 | annotation |
|---|---|---|
| LUSC 6 Marker Set | | |
| cg07113230 | chr1: 8277394-8277395 | LINC01714, |
| cg13886334 | chr2: 175193377-175193378 | LINC01305, |
| cg13906377 | chr1: 63792695-63792696 | FOXD3, FOXD3-AS1, MIR6068, |
| cg02081266 | chr17: 59529618-59529619 | TBX4, |
| cg14587524 | chr19: 38183262-38183263 | ZNF607, ZNF781, |
| cg15576900 | chr1: 44883697-44883698 | RNF220, |
| PAAD 6 Marker Set | | |
| cg03306374 | chr16: 23847325-23847326 | PRKCB, |
| cg14587524 | chr19: 38183262-38183263 | ZNF607, ZNF781, |
| cg25208017 | chr1: 240255486-240255487 | FMN2, |
| cg18375860 | chr1: 237205409-237205410 | RYR2, |
| cg14416371 | chr11: 43602847-43602848 | MIR129-2, |
| cg01893212 | chr7: 49813088-49813089 | VWC2, |
| PCPG 2 Marker Set | | |
| cg14326413 | chr4: 81123380-81123381 | PRDM8, |
| cg03838635 | chr17: 2628322-2628323 | , |
| PRAD 6 Marker Set | | |
| cg11521404 | chr13: 20735532-20735533 | GJA3, |
| cg15071854 | ch r1: 45792688-45792689 | HPDL, |
| cg17355294 | chr19: 51416098-51416099 | KLK4, |
| cg07198194 | chr10: 3109053-3109054 | PFKP, |
| cg24922143 | chr15: 35014270-35014271 | , |
| cg25666433 | chr6: 28367279-28367280 | ZSCAN12, |
| READ 6 Marker Set | | |
| cg06952671 | chr2: 182322268-182322269 | ITGA4, |
| cg08558397 | chr7: 752149-752150 | PRKAR1B, |
| cg15699267 | chr20: 61809557-61809558 | MIR124-3, |
| cg20295442 | chr8: 67344665-67344666 | ADHFE1, RRS1, RRS1-AS1, |
| cg14015706 | chr9: 132382433-132382434 | C9orf50, NTMT1, |
| cg00421139 | chr8: 97172961-97172962 | GDF6, |
| SKCM 6 Marker Set | | |
| cg21889472 | chr5: 42992555-42992556 | FLJ32255, |
| cg13255096 | chr6: 137112939-137112940 | MAP3K5, |
| cg16838838 | chr2: 85641023-85641024 | CAPG, |
| cg09923107 | chr20: 30193892-30193893 | ID1, |
| cg02085210 | chr2: 10589054-10589055 | LOC101929715, ODC1, SNORA80B, |
| cg08195943 | chr3: 129694487-129694488 | TRH, |
| STAD 6 Marker Set | | |
| cg01423964 | chr1: 111217575-111217576 | KCNA3, |
| cg17373442 | chr3: 142839991-142839992 | CHST2, |
| cg07922007 | chr8: 67874858-67874859 | TCF24, |
| cg21277995 | chr6: 393239-393240 | IRF4, |
| cg08048222 | chr19: 58239012-58239013 | ZNF671, |
| cg09734791 | chr8: 72756155-72756156 | MSC, MSC-AS1, |
| UCEC 6 Marker Set | | |
| cg25060829 | chr6: 28367571-28367572 | ZSCAN12, |
| cg07495363 | chr2: 198651076-198651077 | BOLL, |
| cg27635394 | chr6: 26043820-26043821 | HIST1H2BB, |
| cg18801599 | chr17: 42092187-42092188 | TMEM101, |
| cg09695735 | chr17: 58498977-58498978 | C17orf64, |
| cg16707405 | chr5: 115152413-115152414 | CDO1, |

In summary, we identified optimal sets of six markers for individual cancer types; these marker sets are capable to detect majority of tumors of respective cancer type with high sensitivity and specificity.

Finally, the 1,250 hypermethylated marker CpGs from all cancers and the knowledge about what cancers each marker can detect was used to find a universal set of markers that would be able to identify multiple common cancers. First of all the 1,250 marker CpGs were consolidated to keep the single best marker CpG across all cancer types within a 500 bp locus; this way the set of 1,250 marker CpGs was reduced to 1,114 CpGs. Then, using a similar algorithm as for individual cancers (Materials and Methods), a set of markers was selected that has at least two markers positive in each of 18 cancer types that had hypermethylated markers available (Table 3).

TABLE 3

The universal pan-cancer marker set. Numbers of cancers are counts of the TCGA cancer types for which the marker region have passed the filters.

| Illumina CpG ID | CpG position (hg19) | annotation | Number of cancers |
|---|---|---|---|
| cg01419831 | chr2: 162283705-162283706 | TBR1 | 10 |
| cg03217795 | chr16: 23847556-23847557 | PRKCB | 8 |
| cg08189989 | chr2: 105459164-105459165 | LINC01158 | 7 |
| cg14416371 | chr11: 43602847-43602848 | MIR129-2 | 6 |
| cg16306898 | chr1: 1475675-1475676 | TMEM240 | 6 |
| cg08195943 | chr3: 129694487-129694488 | TRH | 6 |
| cg14587524 | chr19: 38183262-38183263 | ZNF607, ZNF781 | 6 |
| cg22538054 | chr12: 95941988-95941989 | USP44 | 4 |
| cg22524657 | chr1: 47999163-47999164 |  | 3 |
| cg04066019 | chr3: 16554466-16554467 | RFTN1 | 3 |
| cg14326413 | chr4: 81123380-81123381 | PRDM8 | 2 |
| cg03838635 | chr17: 2628322-2628323 |  | 1 |

When this 12 marker set was tested across all 33 TCGA cancer types it was found that, in addition to cancers it was derived from, this marker set can identify, with high sensitivity and specificity, tumors belonging to additional cancer types. This universal set can identify tumors from 18 cancer types that were represented in the source marker CpG pool with AUC 0.99 or higher. In addition it can identify the other 15 cancer types that were not represented in the source marker pool with AUCs ranging from 0.84 to 1.00 (Table 4).

TABLE 4

Areas under the curve (AUC) for the universal pan-cancer marker set across all 33 TCGA tumor cohorts using the normal whole blood cohort (n = 1,388) as a control.

| TCGA Cancer Type | AUC |
|---|---|
| ACC | 0.978 |
| BLCA | 0.999 |
| BRCA | 1.000 |
| CESC | 1.000 |
| CHOL | 0.999 |
| COAD | 1.000 |
| DLBC | 0.995 |
| ESCA | 1.000 |
| GBM | 0.999 |
| HNSC | 1.000 |
| KICH | 0.937 |
| KIRC | 0.973 |
| KIRP | 0.918 |
| LAML | 0.905 |
| LGG | 0.998 |
| LIHC | 0.998 |
| LUAD | 1.000 |
| LUSC | 0.999 |
| MESO | 0.983 |
| OV | 0.844 |
| PAAD | 0.999 |
| PCPG | 0.998 |
| PRAD | 0.998 |
| READ | 1.000 |
| SARC | 0.956 |
| SKCM | 0.999 |
| STAD | 1.000 |
| TGCT | 0.851 |
| THCA | 0.871 |
| THYM | 0.871 |
| UCEC | 0.998 |
| UCS | 1.000 |
| UVM | 0.955 |

Figure 4:
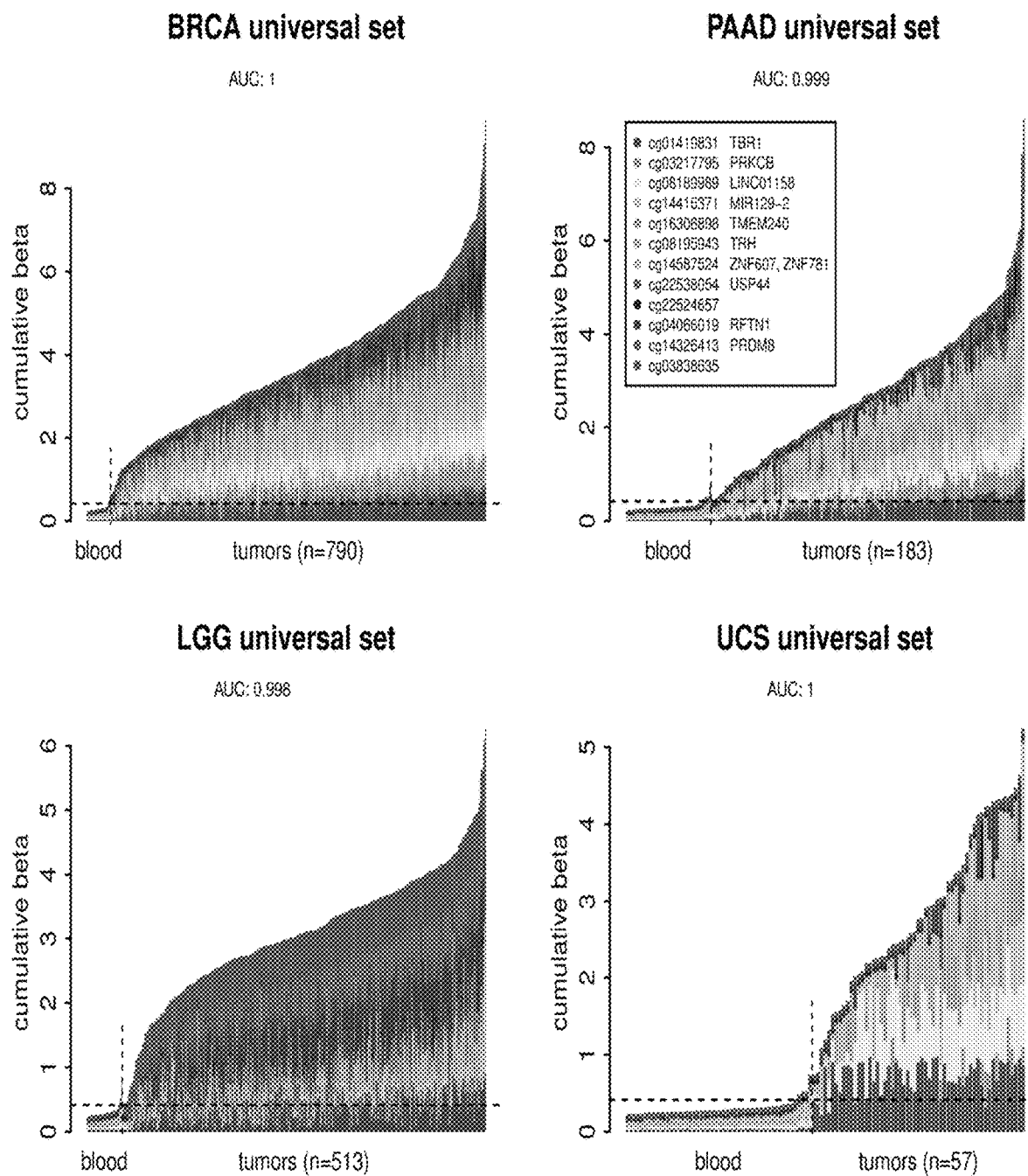
FIG. 4 illustrates the performance of the universal marker set on examples of four cancer types. The BRCA and PAAD are cancers that had specific markers in the pool from which the universal set was chosen. The LGG and UCS are cancers that did not have markers in that pool since there were no normal samples available for these cancers; nonetheless the universal marker set is able to identify these cancers with high sensitivity and specificity. The plots show DNA methylation of the universal marker set in individual tumor samples in comparison to normal blood samples. Only 50 randomly chosen blood samples out of the whole control blood cohort are shown. The horizontal dashed line shows the $95^{th}$ percentile of the cumulative DNA methylation of the marker set in the entire control normal blood cohort (n=1,388). The AUC was calculated using the whole tumor cohort and the whole normal blood cohort (n=1,388) for each cancer type.
Figure 5:
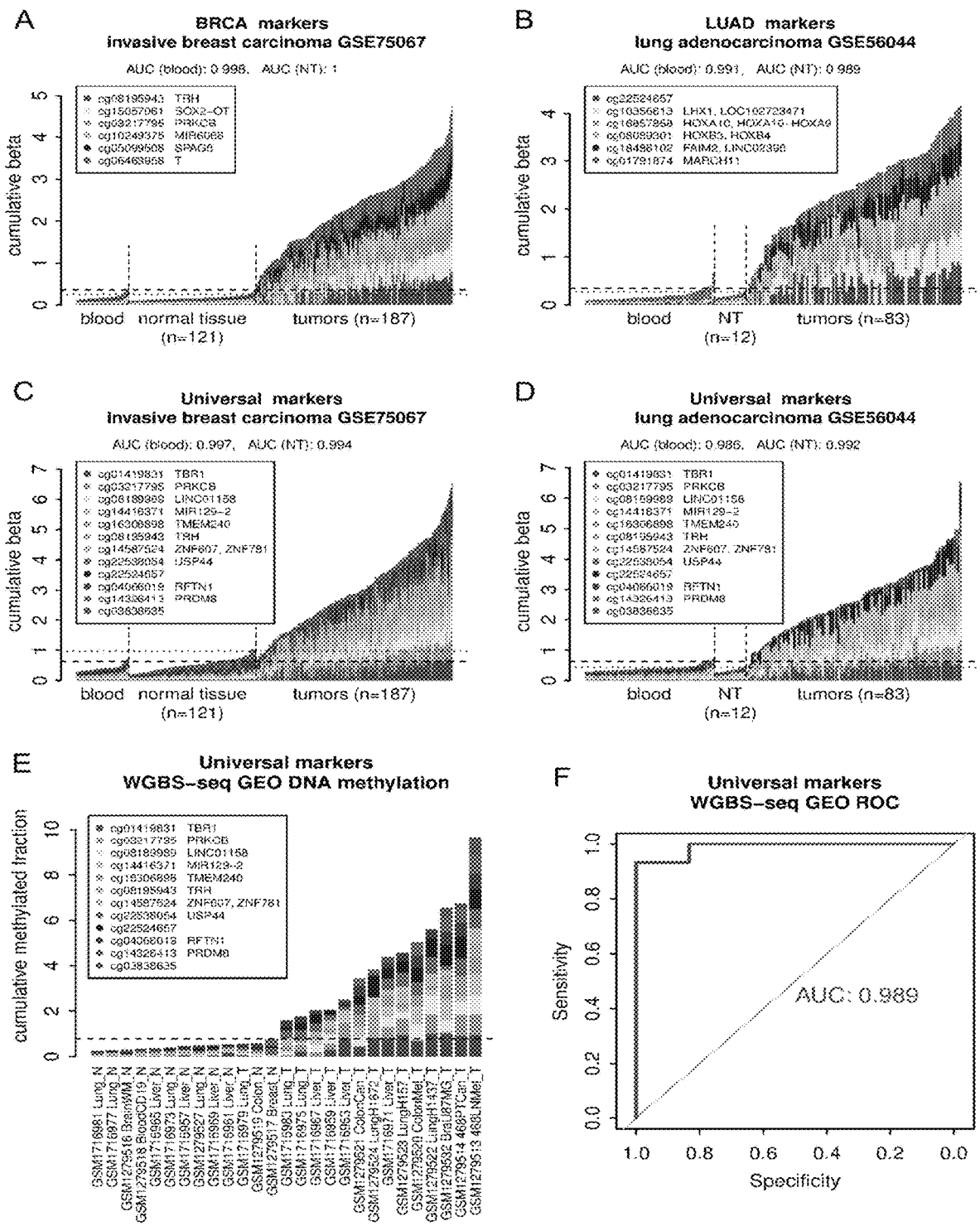
FIG. 5 shows validation of marker sets identified using TCGA data on independent sample cohorts from the GEO. (a) The BRCA specific six marker set was tested using independent invasive breast carcinoma cohort (GSE75067). (b) The LUAD specific six marker set was tested using independent lung adenocarcinoma cohort (GSE56044). (c,d) Both of these cohorts were also used to test the universal marker set. Normal whole blood cohort (GSE72775) and respective normal tissues (NT, breast GSE101961, lung GSE56044) were used as controls. The plots show DNA methylation of each marker set in individual tumor samples in comparison to normal blood samples and respective NT samples. Only 50 randomly chosen blood samples are shown. The horizontal dashed and dotted lines shows the 95th percentile of the cumulative DNA methylation of each marker set in the entire normal blood cohort (n=335) and in respective NT cohort, respectively. The AUCs were calculated using the whole tumor cohort and the whole normal blood cohort (n=335) or respective NT as a normal reference for each cancer and marker set combination. (e) Validation of the universal marker set using whole genome bisulfate sequencing (WGBS-seq) data from GEO (GSE52271, GSE56763, GSE70090). The mean methylated fraction for 200 bp regions matching the marker CpGs was calculated from the WGBS-seq data and then used in a similar way as beta values in previous analysis. Individual samples are labeled by their GEO accession and an abbreviation of the tissue or cell line, N or T at the end denominates normal or tumor samples, respectively. The horizontal dashed line shows the maximum of the cumulative DNA methylation of the marker set in the normal samples. (f) ROC analysis curve for the universal marker set and WGBS-seq cohort from (e).

FIG. 4 shows the performance of the universal marker set for two cancers that were represented in the pool it was derived from (BRCA and PAAD) and two additional cancer types that were not represented in the marker source pool (brain lower grade glioma (LGG) and uterine carcinosarcoma (UCS)). Overall, we found a universal marker set that can detect tumors of most TCGA cancer types with high sensitivity and specificity.

We validated the discovered marker sets on independent datasets. Although the fact that the universal marker set can identify tumor types that were not used in its discovery suggests universal performance, we decided to test the markers on completely independent data to make sure they will perform universally. For this testing we used HumanMethylation450 data from additional cohorts of normal blood and tumor samples from the GEO database. A normal blood cohort of 335 samples (GSE72775) was used as an independent cancer free control and invasive breast carcinoma (GSE75067) and lung adenocarcinoma (GSE56044) cohorts were used to test BRCA and LUAD six marker sets, respectively, as well as the universal marker set. In addition to normal blood samples, tumor samples were tested against references from respective normal tissues (NT). The lung dataset had its own set of normal lung tissue samples and for the breast cohort normal breast samples from GSE101961 were used. The results (FIG. 5A-D) show good performance of all three marker sets (AUC blood: 0.986-0.998, AUC NT: 0.989-1.0), indicating that the marker sets discovered from TCGA tumor data using our approach would likely identify any independent tumors of the type they were designed for. To validate the markers using data from other analytical platform than Illumina HumanMethylation450, we have tested the universal marker set on the whole genome bisulfite sequencing (WGBS-seq) data from GEO. Samples from two studies 32(datasets GSE52271 and GSE56763, 5 normals, 8 tumors) and 33(dataset GSE70090, 7 normals, 7 tumors) were combined into one cohort and analysis was performed on cumulative methylated fraction of 12 genomic regions corresponding to the universal marker set.

The results (FIG. 5 E, F) are in good agreement with the results from HumanMethylation450 data, AUC=0.989, 14 out of 15 tumor samples were classified as tumors. In summary, using independent GEO data cohorts from Illumina HumanMethylation450 platform and also from autonomous WGBS-seq analytical platform we successfully validated marker sets discovered based on the TCGA data. The new discovered markers will broaden the spectrum of tumor types that could be diagnosed and monitored from liquid biopsies and other minimally invasive samples including, for example, blood, lymph, urine, stool, and saliva.

An additional set of 10 DNA methylation markers that can identify tumors of the most relevant 10 TCGA cancer types was selected to be used on clinical samples. The set of multiple markers rather than a single marker has several advantages. First, using multiple markers will increase the probability that at least some of the markers are methylated in particular tumor that needs to be detected. Second, a marker set could be designed to identify multiple cancer types that may differ in regions that are constitutively hypermethylated. Third, multiple markers increase sensitivity of the test since multiple genomic regions are tested that effectively increases the amount of available cancer specific template for the assay in a limited volume of a typical plasma sample. The original suite of 1,250 markers was used to select an optimal set of markers that can identify tumors of 10 TCGA cancer types (BLCA, BRCA, COAD, ESCA, HNSC, LUAD, LUSC, PAAD, PRAD, READ) that are most relevant for our field of study.

For reference throughout this specification, Table 5 (below) shows the list of the 10 marker loci of the marker set that detect 10 most relevant TCGA cancer types. Columns 4-13 indicate for which cancer types has particular marker passed all the original marker filtering criteria. Annotation column indicates overlapping or nearby located genes.

findings show that the selected 10 marker set can very well differentiate tumor specific DNA from DNA originating from normal blood or normal tissue samples. In summary we have chosen optimal marker set to detect DNA methylation in 10 TCGA cancer types and verified that these markers can distinguish tumor derived DNA from DNA originating from normal cells.

The next step after the validation of the marker set using data from tumor tissue samples was to determine how the markers will perform on cfDNA from clinical blood samples. In order to be able to detect very small amounts (several copies) of tumor specific methylated DNA that could be found in cfDNA, quantitative PCR specific to methylated marker regions was used. Ten qPCR amplicons specific for 10 marker loci and three qPCR amplicons specific for universally methylated loci that serve as load controls were designed. The pairs of primers and the probes for qPCR amplicons were designed to be specific for the methylated sodium bisulfite treated DNA. The amplicons were selected to overlap or be as close as possible to the marker CpGs determined by the Illumina HumanMethylation450 microarray listed in Table 5. The size of the amplicons was designed to be as short as possible (65-90 bp) to perform well on the fragmented templates like cfDNA.

| Illumina.CpG.ID | CpG.position (hg19) | annotation | BLCA | BRCA | COAD | ESCA | HNSC | LUAD | LUSC | PAAD | PRAD | READ |
|---|---|---|---|---|---|---|---|---|---|---|---|---|
| cg14416371 | chr11: 43602847-43602848 | MIR129-2 | 0 | 1 | 0 | 1 | 1 | 1 | 0 | 1 | 0 | 0 |
| cg08189989 | chr2: 105459164-105459165 | LINC01158 | 1 | 1 | 1 | 1 | 0 | 0 | 1 | 0 | 0 | 1 |
| cg00100121 | chr1: 169396635-169396636 | CCDC181 | 0 | 1 | 1 | 0 | 1 | 0 | 0 | 0 | 1 | 1 |
| cg03306374 | chr16: 23847325-23847326 | PRKCB | 0 | 1 | 1 | 0 | 0 | 0 | 0 | 1 | 1 | 0 |
| cg01419831 | chr2: 162283705-162283706 | TBR1 | 1 | 1 | 1 | 0 | 1 | 1 | 1 | 0 | 0 | 0 |
| cg25875213 | chr19: 38183055-38183056 | ZNF781 | 0 | 0 | 0 | 1 | 1 | 0 | 1 | 1 | 0 | 0 |
| cg00339556 | chr5: 16180048-16180049 | MARCH11 | 1 | 0 | 1 | 1 | 1 | 1 | 0 | 0 | 0 | 1 |
| cg01893212 | chr7: 49813088-49813089 | VWC2 | 0 | 0 | 1 | 0 | 0 | 0 | 0 | 1 | 1 | 1 |
| cg14732324 | chr5: 528621-528622 | SLC9A3 | 1 | 0 | 1 | 0 | 1 | 1 | 0 | 0 | 0 | 0 |
| cg07302069 | chr7: 27196286-27196287 | HOXA7 | 0 | 0 | 0 | 0 | 0 | 0 | 1 | 0 | 1 | 0 |

Figure 6:
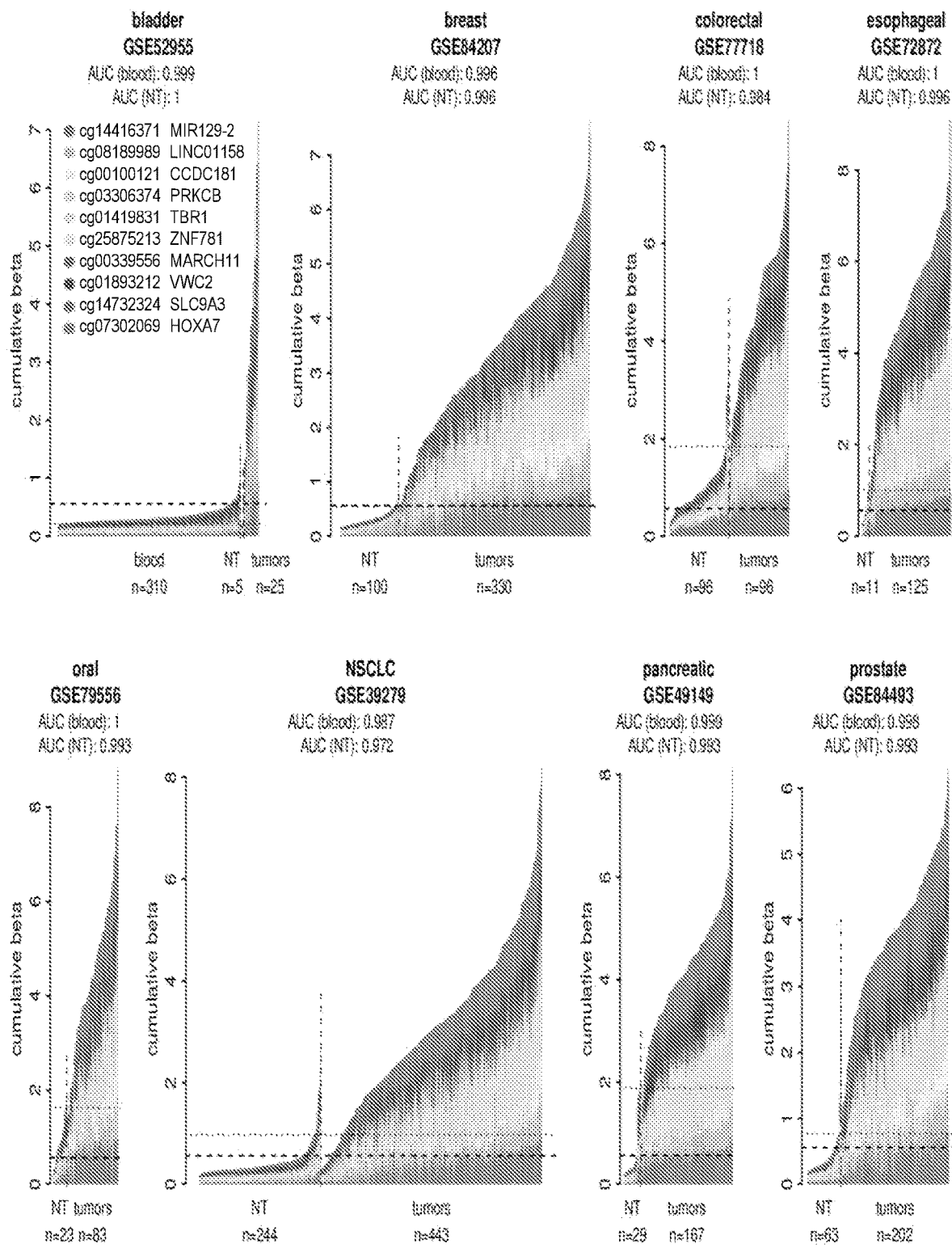
FIG. 6 shows the validation of the 10 marker set on independent cancer sample cohorts from the GEO. The eight cancer types shown here represent 10 TCGA cancer types for which the marker set was designed. Normal whole blood cohort (GSE72773, n=310) and respective normal tissues (NT) were used as controls. The plots show DNA methylation of the marker set in individual tumor samples in comparison to normal blood samples and respective NT samples. The DNA methylation data from the normal blood cohort are shown only in the first panel and in the additional panels the 95th percentile of the cumulative DNA methylation of the normal blood cohort is represented by the horizontal dashed lines. The horizontal dotted lines indicate the 95th percentiles of the cumulative DNA methylation of the respective NT cohorts. The AUCs were calculated using the respective tumor cohort and the normal blood cohort or respective NT as a normal reference for each cancer cohort.

This optimal set contains 10 markers and based on the original marker filtering criteria each out of 10 cancer types is represented by at least four markers (see Table 5). This marker set was then tested and validated using independent data from GEO database. Eight GEO cancer sample cohorts (total n=1,471) representing 10 TCGA cancer types were tested against normal blood GEO samples (n=310) as well as respective normal tissue GEO samples (total n=571). The results confirmed that this 10 marker set can identify, with high sensitivity and specificity (blood reference: AUC 0.987-1.0; respective normal tissue reference: AUC 0.972-1.0), all cancers it was designed for (see FIG. 6). These Since the amount of tumor specific DNA in blood is typically very low, a two-step qPCR reaction was chosen as the analytical strategy to reduce stochastic effects of low numbers (FIG. 7). In the first step the whole amount of sodium bisulfite-treated cfDNA extracted from 2 ml of plasma is amplified in a multiplex reaction using 13 primer pairs (see Table 6 below) for all amplicons in a single tube and 15 cycles of PCR. The reaction product is then diluted 200 fold and used in the second step—a standard qPCR which consists of individual reactions for individual amplicons. This way even the cancer specific templates present only in several copies have a chance to be detected since all the templates are equally pre-amplified before the samples are divided into individual amplicon specific reactions for quantification.

TABLE 6

| Name | Forward primer | Seq ID No. | Reverse primer | Seq ID No. |
|---|---|---|---|---|
| Markers: | | | | |
| MIR129-2 (amplicon 70bp) | GTTCGGTTTTAGGGTTCGGAGAT | 1 | CAAAATATACCGACTTCTTCGATTCG | 14 |
| LINC01158 (amplicon 86bp) | TTTTATAGGGGTAGCGATTAGCGTTG | 2 | CTCTAAAACGCGCTCACCGAAA | 15 |
| CCDC181 (amplicon 87bp) | GGATATTGTATGCGTTTGCTAGATT | 3 | CATAACAACAACGTACCTCTACGTCCTC | 16 |
| PRKCB (amplicon 71bp) | CGGGCGAAGCGTACGGTGT | 4 | CGCAAAATAACTAACCCGACTACGA | 17 |
| TBR1 (amplicon 73bp) | TGCGTTTTATCGATCGTACGTGTT | 5 | CCCGACTACGCTCCTCCGAC | 18 |
| ZNF781 (amplicon 78bp | GATTTAGTAGTCGTTGGTATAAGTTGCGT | 6 | CGATAAATCCGCGCACTCGAA | 19 |
| MARCH11 (amplicon 89bp) | CGTTTCGGAATCGACGTGAGC | 7 | AAATTCGACTCCGAACGAACGA | 20 |
| VWC2 (amplicon 70bp) | AGTGATAGGTTGGTTCGGCGTAGT | 8 | CTCGCGCTACCCCCGAAA | 21 |
| SLC9A3 (amplicon 79bp) | CGGTCGGTTACGTCGTCGAAT | 9 | CAACGAAACGAAAACGATTACGAA | 22 |
| HOXA7 (amplicon 68bp) | TTGAGATTGGCGGAGGCGGTT | 10 | CCATTTTCTTTTAAACGAAACTCGC | 23 |
| Controls: | | | | |
| LRRC8A (amplicon 81bp) | TTGTATTTGACGGGTAATTTGAGCG | 11 | CTTAAAACGTTTAAACTCCCGCAAC | 24 |
| NCOR2 (amplicon 74bp) | GGGTTTTAGTTCGGAGCGGGT | 12 | GACCAAAACGACCCCGAACAA | 25 |
| TRAP1 (amplicon 68bp) | GGTGACGGTTGGGGCGTAT | 13 | AAAATACGCCAACCGCATACGA | 26 |

| Name | Seq ID No. | Probe sequence |
|---|---|---|
| Markers: | | |
| MIR129-2 (amplicon 70bp) | — | Roche UPL70 |
| LINC01158 (amplicon 86bp) | 27 | TTTGGGTCGGGTTGGGTCGTTT |
| CCDC181 (amplicon 87bp) | 28 | TCGTTTTCGTAGTTAGAGAGGTTCGGATG |
| PRKCB (amplicon 71bp) | — | Roche UPL70 |
| TBR1 (amplicon 73bp) | — | Roche UPL70 |
| ZNF781 (amplicon 78bp | 29 | CGGAGACGTGGGAGCGTTTTTTG |
| MARCH11 (amplicon 89bp) | 30 | TCGGTTCGTGGAGGCGGTT |
| VWC2 (amplicon 70bp) | 31 | AACCCTACCGCCGCACCCGCT |
| SLC9A3 (amplicon 79bp) | 32 | CGTTATGGGTTTTTTTCGTATTCGTATGT |
| HOXA7 (amplicon 68bp) | 33 | TGTGGGCGGTTACGTGTTGCG |

TABLE 6-continued

Controls:

| Name | SEQ ID | Sequence |
|---|---|---|
| LRRC8A (amplicon 81bp) | 34 | GGAGAATAATCGTTATATCGTTATCGACGG |
| NCOR2 (amplicon 74bp) | 35 | TTTGGCGAGGAAGGTATGGTCGGT |
| TRAP1 (amplicon 68bp) | 36 | GGTAGTAGATGTTGCGGGTGTCGGT |

Figure 8:
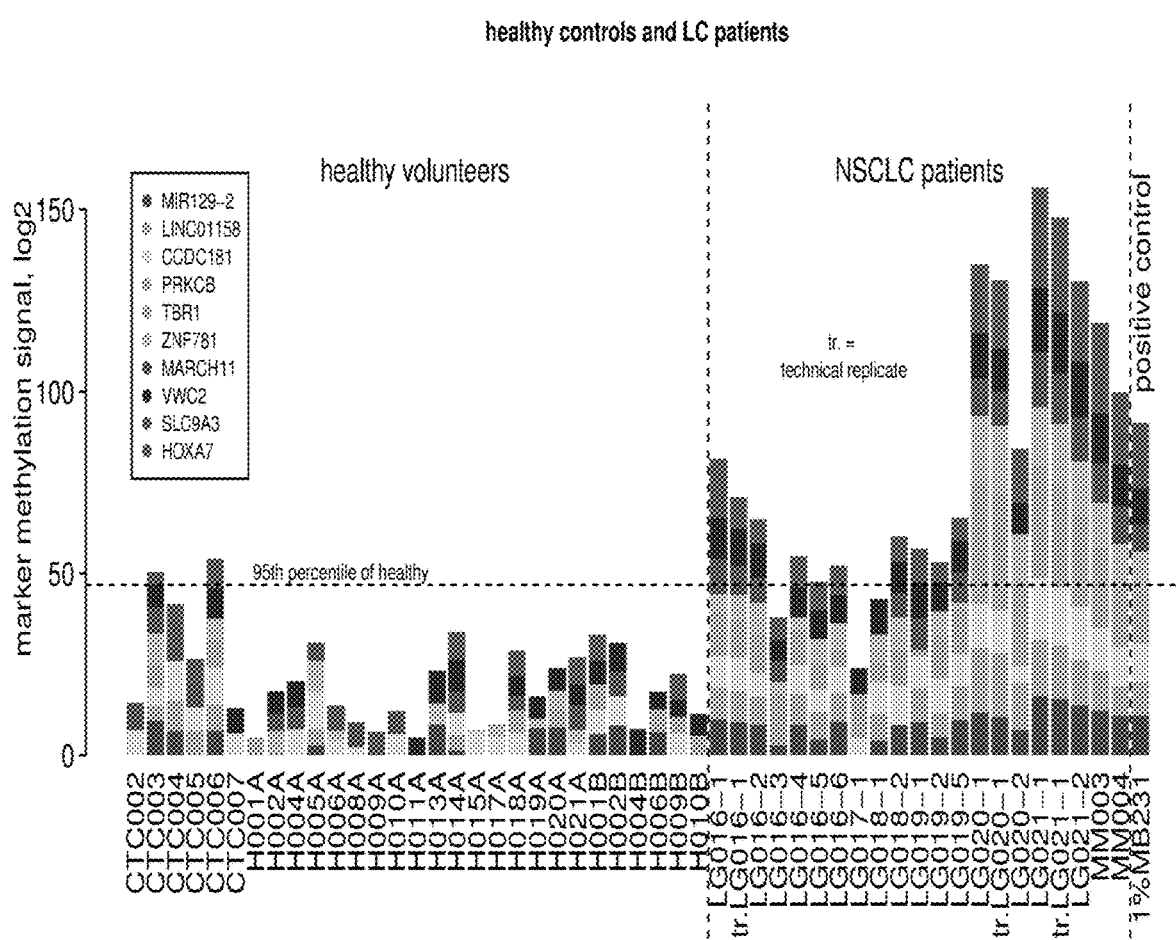
FIG. 8 shows DNA methylation signal from the whole 10 marker set on a cohort of 29 healthy subjects (left part) and several lung cancer patients undergoing cancer treatment (right part). The patient data include multiple draws from the same subjects and also three technical replicates. The very last sample on the right is a level of signal from positive control that consist of 20 ng of normal blood DNA spiked with 200 pg of DNA from tumor cell line MDA-MB231 that has all 10 markers methylated. This amount of DNA (20 ng) mimics typical amount of cfDNA in 2 ml of plasma in healthy subjects. The 200 pg (1%) of added MDA-MB231 DNA imitates situation when each marker in sample is 1% methylated.
Figure 9:
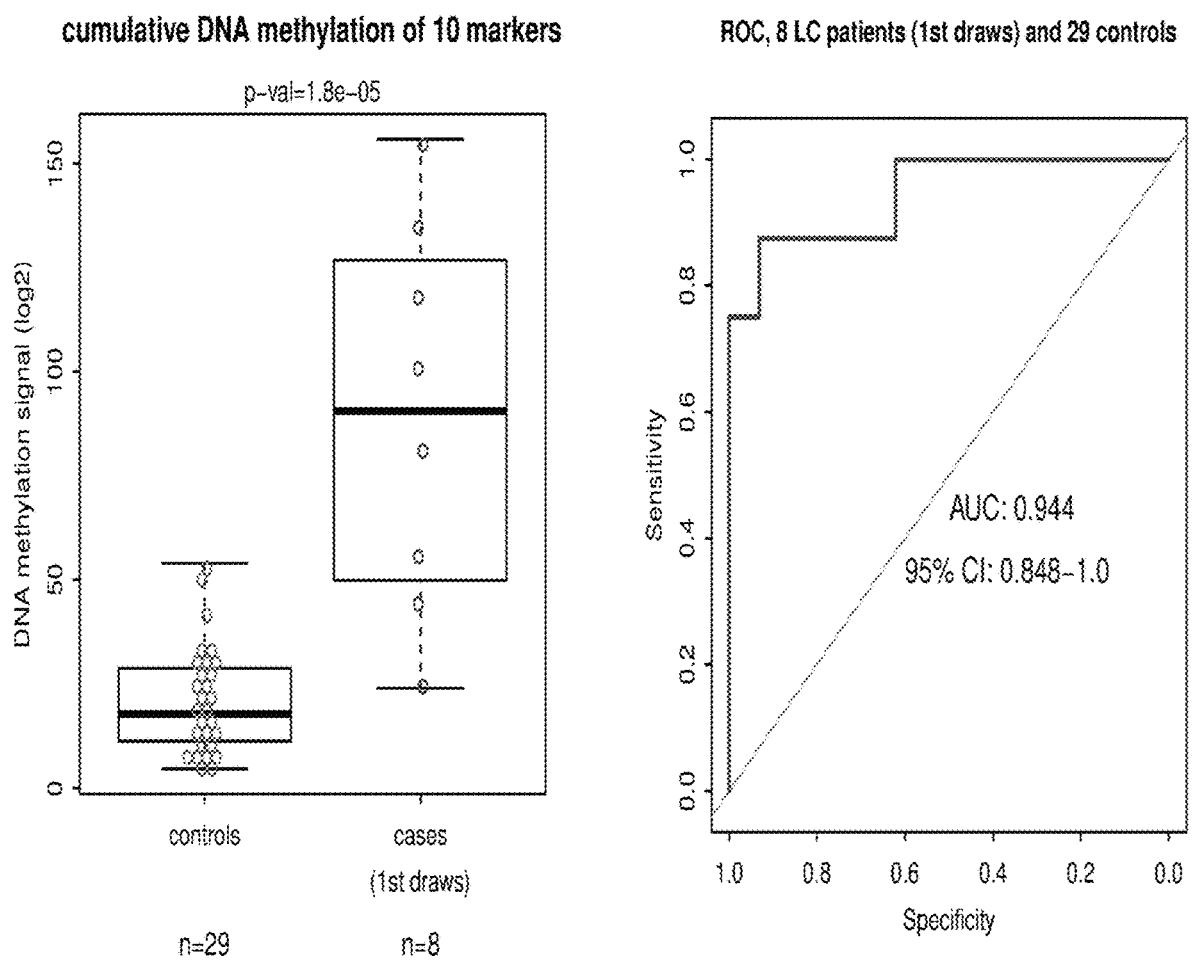
FIG. 9 depicts patient data. The left panel shows cumulative DNA methylation signal from all 10 marker loci for the control group of 29 healthy volunteers and for a group of lung cancer cases. The cases group consists only of the first available blood draws from 8 NSCLC patients undergoing treatment. P-value shown is for Wilcoxon rank sum test. The right panel shows the receiver operating characteristic (ROC) analysis of the marker set signal from 29 controls and 8 NSCLC cases. AUC—area under the curve, CI—confidence interval.

Using the above described approach we then analyzed cfDNA from plasma samples obtained from 29 healthy volunteers and several lung cancer patients undergoing cancer treatment. While cfDNA from healthy donors is showing overall low background DNA methylation across the marker set, the cancer patient samples have overall higher level of the DNA methylation signal and a substantial fraction of the patients shows high level of DNA methylation across majority of the markers (FIG. 8). The distribution of the cumulative DNA methylation signal from all markers in the group of the first available blood draws from 8 individual NSCLC patients (cases) is highly significantly different (p-value=$1.8 \times 10^{-5}$) from the group of 29 healthy volunteer individuals (controls) (FIG. 9). The ROC analysis using the 29 controls and 8 cases revealed quite large area under the curve (AUC=0.944) with 95% confidence interval 0.848-1.0 (FIG. 9). These findings clearly illustrate that the 10 marker set and the detection technique employed are able to distinguish between healthy individuals and lung cancer cases with high sensitivity and specificity. The samples from additional subjects are currently analyzed and as data from more cancer cases are available it will allow thresholds that would be suitable for diagnostics to be determined.

In summary, genomic regions with cancer specific changes in DNA methylation that could be used to detect and monitor multiple cancers from cfDNA samples were determined. The study used TCGA HumanMethylation450 data, the largest collection of tumor DNA methylation data available with over 8,500 tumor samples. First, for each cancer type, DMRs were identified and those were then further filtered against cohorts of normal tissue samples to obtain regions suitable as cancer markers. From the pools of filtered marker regions were selected optimal cancer specific sets of markers as well as the universal marker set that could identify tumors of most cancer types.

Blood and other body fluids provide means for easy, cost effective, minimally invasive diagnosis of diseases including cancer. Blood samples are used to diagnose cancer by detecting tumor specific changes in DNA present in cfDNA. Our study was focused on finding marker regions with tumor specific changes in DNA methylation. Aberrant DNA methylation typically occurs at multiple loci in majority of tumors and therefore has potential for higher sensitivity than, e.g. cancer specific mutations. We found sets of DNA methylation marker regions for 18 TCGA cancer types and a universal set of markers for all 33 cancer types. These markers could be potentially used for cancer diagnosis and monitoring of treatment or cancer recurrance from blood samples.

Currently, there are a few DNA methylation markers in clinical use for cancer diagnosis from cfDNA. One, SEPT9 promoter region of the v2 transcript was identified as possible colorectal cancer marker and developed into clinically used test to identify colorectal cancer from plasma samples. In our study this SEPT9 region was identified in a broader selection as a marker for COAD, READ and HNSC. In HNSC SEPT9 is the first of the markers in the optimal set selected to identify majority of HNSC tumors. A second clinically used marker, located in promoter CpG island of GSTP1, was first identified as tumor marker in prostatic carcinomas and later developed to detect prostate cancer from urine or blood samples. Our pool of 157 prostate cancer markers includes GSTP1. The fact that our approach identified markers currently in clinical use, in addition to hundreds of new marker regions, indicates validity of our approach and the great potential of the newly identified markers. These new markers will substantially expand the capability of blood sample based cancer diagnosis and monitoring to a broader spectrum of cancers.

The discovered DMRs (FIG. 1) and also the filtered markers (FIG. 2) are predominantly regions hypermethylated in cancers, but unmethylated in normal tissues. This is in contrary to knowledge that most of the genome of cancer cells is hypomethylated. However, the Illumina HumanMethylation450 platform covers only about 450 thousand CpGs out of 28 million CpGs of the human genome with focus on CpG islands and gene promoters—genomic features that are typically unmethylated in normal cells and hypermethylated in cancer cells. This explains why large fraction of hypermethylated marker regions was identified. The hypermethylated regions are more suitable as markers.

Cancer specific hypermethylation typically occurs in GpC rich regions like CpG islands, while hypomethylation is occurring in CpG poor regions. The size of the amplicon for the DNA methylation analysis should be as small as possible to utilize fragmented cfDNA as a template and at the same time it should contain multiple CpGs to efficiently differentiate between methylated and unmethylated variant. Therefore hypermethylated regions with their high CpG density are more suitable for such analysis. In addition DNA methylation analysis starts from bisulfite converted DNA where methylated cytosines are resistant to this conversion. Consequently methylated DNA retains higher complexity after bisulfite conversion, which is preferable for specific amplicon design. Therefore the large fraction of identified hypermethylated markers could be considered an advantage.

Some cancer types e.g. COAD, rectum adenocarcinoma (READ), CESC, head and neck squamous cell carcinoma (HNSC) and PRAD have much larger numbers of hypermethylated markers after filtering than others (FIG. 2). This could be due to several factors. 1) These cancers could have a larger fraction of aberrant DNA methylation than other cancers. 2) Some of these tumor samples are more pure i.e. contain only small proportion of non-tumor cells and therefore the DNA methylation data are less diluted and more regions pass the stringent filters. 3) Some other cancers e.g. BRCA are more heterogeneous and therefore there are fewer markers that would be hypermethylated across most of the tumors of the particular type, which again can lead to filtering out some of the regions.

Our study was focused on markers for the individual cancer types as well as pan-cancer type markers, but has not sought markers specific for individual cancer subtypes. Since this is an in silico study based on the data from tumor samples and normal tissues, performance for the individual cancer types will differ for clinical cfDNA samples. Some tumor types that appear to be easy to detect in silico might be harder to detect in cfDNA due to a low amount of tumor DNA they contribute to cfDNA and vice versa, some tumors that might not look easy to be detected due to dilution of tumor samples with normal cells in TCGA data might be relatively easy to detect in cfDNA if they contribute a significant fraction to the cfDNA pool. Another important factor in marker performance will be disease stage; tumors with higher disease stage will likely leave stronger methylation footprint within cfDNA. Therefore the level of the detected DNA methylation signal could be potentially used to estimate disease stage and or tumor burden in case of monitoring recurrent disease. Overall, the clinical performance of the discovered markers in various cancers will likely depend on additional factors in addition to their in silico performance.

The identified marker regions contain a substantial fraction of genes annotates as noncoding RNA. These noncoding RNA genes include several miRNA genes, consistent with our previous findings that miRNA genes are frequent targets of aberrant DNA methylation in cancer. Indeed, one of the best markers, hypermethylated in a large fraction of tumors in multiple cancers and one of the markers of the universal pan-cancer set, is MIR129-2. MicroRNA 129 has tumor suppressive role and MIR129-2 gene was previously shown to be hypermethylated in multiple cancers. Other miRNA gene markers in selected marker sets are MIR124-3, which was also reported hypermethylated in several cancers, and MIR6068. In addition to miRNA genes, a fraction of markers in individual sets are regions annotated as long noncoding RNAs. Besides the utility of these noncoding regions as DNA methylation cancer markers, these findings further support importance of epigenetic deregulation of the noncoding part of the genome in carcinogenesis.

Multiple studies about discovery and testing of cancer specific DNA methylation markers were published in recent years, most of them focused on a single cancer type. Several studies were published on markers for breast cancer, colorectal cancer, lung cancer or pancreatic cancer. A very recent study used TCGA Illumina HumanMethylation450 data from seven cancer types to build a model that could be used to predict cancer status based on low coverage whole genome bisulfite sequencing (WGBS) data from cfDNA. This approach requires preparation and sequencing of bisulfite converted libraries from each cfDNA sample compared to our study, which found sets of several marker regions that could be analyzed by qPCR or ddPCR. Overall, compared to other studies seeking methylation cancer markers, our study is unique due to its pan-cancer approach and focus on several markers that could identify most cancers.

In summary, using TCGA Illumina HumanMethylation450 data for all available TCGA cancer types we identified sets of genomic regions specifically methylated in majority of tumor samples that could be used as markers for noninvasive cancer detection and monitoring. To our knowledge this is the first comprehensive pan-cancer tumor methylation marker discovery study performed so far using the largest set of tumor data (>8,500 tumors) available. The identified marker sets have high sensitivity and specificity in in silico testing on both TCGA data and independent DNA methylation data from the GEO. Clinical testing of these marker regions will likely confirm new markers that could be used for noninvasive diagnosis and monitoring for multiple cancers and thus expand the diagnostic capability of liquid biopsies to a broader spectrum of cancers.

Materials and Methods

The Illumina HumanMethylation450 DNA methylation data for 33 cancer types were downloaded from The Cancer Genome Atlas (TCGA). In addition, the Illumina HumanMethylation450 data for two large normal whole blood sample cohorts (GSE40279, GSE87571-656 and 732 samples, respectively) and several additional normal tissue sample cohorts were downloaded from the GEO (GSE50192, GSE48472, GSE48684, GSE61278, GSE61258, GSE63704, GSE79100, GSE64509, GSE63315, GSE51954, GSE61259, GSE60655, GSE64490, GSE61257, GSE70977). Additional independent sample cohorts of normal whole blood (GSE72775), invasive breast carcinoma (GSE75067), and lung adenocarcinoma (GSE56044) were downloaded from the GEO for marker sets validation. All data were analyzed in the R programming environment using custom scripts (Team RC. R: A Language and Environment for Statistical Computing. Vienna, Austria: R Foundation for Statistical Computing, 2015.). The beta values were first normalized using BMIQ algorithm (Teschendorff AE, Marabita F, Lechner M, Bartlett T, Tegner J, Gomez-Cabrero D, Beck S. A beta-mixture quantile normalization method for correcting probe design bias in Illumina Infinium 450 k DNA methylation data. Bioinformatics 2013; 29:189-96.) custom modified in principal as described (Horvath S. DNA methylation age of human tissues and cell types. Genome Biol 2013; 14:R115.), but using distribution of type I probes from normal breast TCGA samples as a golden standard, separately for type I and type II probes for each sample. This normalization reduced the biases between the two probe chemistries as well as the differences between samples from datasets of different origin.

For each cancer type that had respective non-tumor samples available (23 tumor types), tumor samples were tested relative to respective normal tissue samples. The normalized beta values for individual CpG probes were converted to M values and the limma package was used to determine differentially methylated CpGs. Genomic positional information of the probes was added and overlapping pairs of 2 consecutive covered CpGs up to 500 bp apart were evaluated for differential methylation—mean difference from reference by at least a threshold (0.4 beta). Consecutive CpG pairs that have passed the filter were clustered and these clusters (DMRs) were used as marker candidate regions for further filtering. All CpG probes in candidate clusters were then filtered against methylation in respective and universal normal TCGA cohorts as well as cohorts of normal blood samples and additional normal tissues from the GEO to eliminate candidates with tissue specific methylation. During the filtering the data from the best performing CpG in each candidate region was used to represent the region.

The hypermethylated marker CpGs that passed the filters were further combined to find out optimal sets of markers able to identify the majority of tumor samples for each cancer type and a universal marker set to identify majority of cancers. The selection algorithm worked as follows: The marker was considered positive for certain tumor if the beta of that tumor was at least a threshold (0.3 beta) higher than the 95th percentile of the reference (large blood cohort from cancer free subjects, GSE40279 and GSE87571, n=1388).

Then out of a cohort of tumors were found those identified by the least markers and out of those markers the one with overall best performance (positive in most tumor samples overall) was selected and all tumors identified by this marker were removed from the cohort. The process was repeated until there were no identifiable tumors left. Then all selected markers were removed from the original marker pool and the process was repeated to select additional markers for each tumor sample if desired. Similarly, a universal marker set, that identifies most cancers, was selected using a consolidated pool of all markers from all cancers as a pool to choose from and known information for which cancers each marker passes the filters.

The consolidated pool of all markers was obtained by filtering of all 1,250 hypermethylated marker CpGs, so in cases where different cancers had different CpG representative within the same locus (500 bp) the CpG positive in most cancers was selected as a representative for that locus for all cancers, where any CpG in that locus passed the original filters. Finally, the performance of the marker sets was evaluated using ROC analysis on cumulative beta values for the respective marker set and the large blood sample cohort (n=1388) as a cancer free reference. The ROC analysis and AUC calculations were performed using the package pROC. Marker CpGs used in the figures were annotated by RefSeq gene symbol of the overlapping gene(s) or by genes within 5 kbp of the CpG regardless the direction, if there were no annotated genes within 5 kbp, the marker does not have other identifier than the Illumina CpG ID.

Example 2

A patient enters an oncologic clinic (e.g. standard outpatient or high risk clinic) and is consented for an analysis of their blood and its components for the potential presence of cancer. A 10-20 cc blood sample is collected into Cell-Free DNA BCT blood tubes and the samples are shipped to an appropriately equipped molecular pathology lab. Blood Samples are processed in the laboratory by a technician in a manner that purifies and concentrates cell free DNA (cfDNA) away from the other blood components.

The recovered cfDNA is chemically-modified with sodium bisulfite, purified, and is then ready for DNA methylation analysis using any of a number of analytical platforms, including quantitative real time PCR, digital droplet PCR and next gen DNA sequencing. We currently use quantitative real time PCR. The sodium bisulfite chemical modification of the DNA allows for the downstream determination of the methylation state of any given CpG site in the genome.

Purified, chemically-modified cfDNA is seeded into quantitative real time PCR reactions that contain sequence-specific PCR primers for DNA amplification and sequence-specific probes to detect the target sequences, in addition to standard amplification reagents. The sequence-specific probes may contain locked nucleic acids to increase specificity and sensitivity of detection, and are also fluorescently labeled to allow for quantitation of the PCR products being amplified. This assay is performed in a multiplexed 96-well format. Following PCR, a post-hoc analysis of the assay is performed and a report is prepared for the physician that indicates the presence or absence of tumor with a calculated degree of confidence based on the results of the test. Digital droplet PCR is another technology platform that holds a certain level of appeal for analysis of cfDNA over that of quantitative real time PCR. For example, we predict digital PCR could have increased importance in a scenario where DNA from sentinel lymph nodes is being analyzed. On the plus side of digital droplet PCR, it is anticipated that this technology could increase detection limits by an order of magnitude. On the negative side, the technology would probably be on the order of an order of magnitude more costly.

Other samples can be used. Sentinel lymph nodes of cancer patients are often surgically removed for assessment for the presence of cancer cells in the node, which serves as a marker of tumor metastases, a prognosticator, and a decision point in the cancer treatment tree. Sentinel lymph nodes would be harvested for cellular DNA and then analyzed for the presence of the DNA methylation biomarkers, using the same approaches shown above.

Once a cancer has been diagnosed, many treatment options are available. In some embodiments, cancer detection is followed by one or more treatment steps. Depending on the type, cancer can be treated by one or more of surgery, chemotherapy, radiation therapy, hormonal therapy, targeted therapy (including immunotherapy such as monoclonal antibody therapy) and synthetic lethality, for example.

The biomarkers and methods of the invention can also be used to monitor or detect cancer recurrence, as well as for the monitoring of treatment effectiveness. Thus, for example, the 10 methylation marker set can be used to detect cell free DNA methylation, whereby a decrease or disappearance of detection indicates treatment effectiveness. Conversely, recurrence of a cancer type is indicated if methylation markers for cancer are detected anew.

While the preferred embodiments of the present technology have been illustrated in detail, it should be apparent that modifications and adaptations to those embodiments may occur to one skilled in the art without departing from the scope of the present technology.

What is claimed is:

1. A method of detecting DNA methylation in a sample isolated from a human subject, comprising detecting DNA methylation at CpG sites,
wherein the CpG sites consist of cg14416371, cg08189989, cg00100121, cg03306374, cg01419831, cg25875213, cg00339556, cg01893212, cg14732324 and cg07302069,
wherein the detecting comprises use of primers or probes specific for the CpG sites.

2. The method of claim 1, wherein the detecting comprises one or more of quantitative real time PCR, digital droplet PCR, and next generation DNA sequencing.

3. The method of claim 1, comprising chemically-modifying the DNA with sodium bisulfite and purifying the DNA prior to detecting DNA methylation at the CpG sites.

4. The method of claim 1, comprising processing the DNA to be cell free.

5. A method comprising
(a) chemically modifying cell-free DNA from a liquid biopsy isolated from a human subject with sodium bisulfite to create chemically-modified DNA,
(b) amplifying the chemically-modified DNA corresponding to CpG sites with primers specific for the chemically-modified DNA
wherein the CpG sites consist of cg14416371, cg08189989, cg00100121, cg03306374, cg01419831, cg25875213, cg00339556, cg01893212, cg14732324, and cg07302069, and
(c) detecting the amplified DNA.

6. The method of claim 5, wherein (b) comprises a multiplex PCR reaction comprising amplifying the chemically-modified DNA with ten primer pairs, wherein each of the ten primer pairs is specific for the chemically-modified DNA sequence corresponding to the CpG site of one of each of cg14416371, cg08189989, cg00100121, cg03306374, cg01419831, cg25875213, cg00339556, cg01893212, cg14732324, and cg07302069 in a single reaction volume to form a reaction product comprising the amplified DNA.

7. The method of claim 6, wherein (b) further comprises using the reaction product as a substrate for ten separate PCR reactions, wherein each individual PCR reaction comprises a single primer pair for the chemically-modified DNA sequence corresponding to the CpG site of one of each of cg14416371, cg08189989, cg00100121, cg03306374, cg01419831, cg25875213, cg00339556, cg01893212, cg14732324, and cg07302069.

8. The method of claim 5, wherein the PCR is quantitative real time PCR.

9. The method of claim 5, wherein (b) comprises ten separate PCR reactions, wherein each individual PCR reaction comprises a single primer pair for the chemically-modified DNA sequence corresponding to the CpG site of one of each of cg14416371, cg08189989, cg00100121, cg03306374, cg01419831, cg25875213, cg00339556, cg01893212, cg14732324, and cg07302069.

* * * * *